US008686335B2

(12) United States Patent
Schmid et al.

(10) Patent No.: US 8,686,335 B2
(45) Date of Patent: Apr. 1, 2014

(54) SYSTEM AND METHOD FOR ADJUSTING THE LIGHT OUTPUT OF AN OPTOACOUSTIC IMAGING SYSTEM

(75) Inventors: Gregory Schmid, San Antonio, TX (US); Bryan Clingman, Chandler, AZ (US)

(73) Assignee: Seno Medical Instruments, Inc., San Antonio, TX (US)

( * ) Notice: Subject to any disclaimer, the term of this patent is extended or adjusted under 35 U.S.C. 154(b) by 236 days.

(21) Appl. No.: 13/341,950

(22) Filed: Dec. 31, 2011

(65) Prior Publication Data
US 2013/0168532 A1   Jul. 4, 2013

(51) Int. Cl.
*G01J 1/32* (2006.01)
(52) U.S. Cl.
USPC ........................................ 250/205; 250/208.1
(58) Field of Classification Search
USPC .......... 250/205, 208.1, 214 R, 370.09, 459.1, 250/458.1, 363.01; 600/160–182, 476–478
See application file for complete search history.

(56) References Cited

U.S. PATENT DOCUMENTS

| 5,460,182 A | 10/1995 | Goodman et al. |
|---|---|---|
| 6,617,559 B1 * | 9/2003 | Emery et al. ................. 250/205 |
| 7,741,900 B1 | 6/2010 | Li |
| 2006/0167531 A1 | 7/2006 | Gertner et al. |
| 2008/0255433 A1 | 10/2008 | Prough et al. |
| 2010/0285518 A1 | 11/2010 | Viator et al. |

OTHER PUBLICATIONS

ISA/US, International Search Report, Int'l Application No. PCT/US12/72277, Mar. 19, 2013, p. 5.

* cited by examiner

*Primary Examiner* — Que T Le
(74) *Attorney, Agent, or Firm* — Greenberg Traurig, LLP

(57) ABSTRACT

A system and method for adjusting the light output of an optoacoustic imaging system. An optoacoustic imaging system includes a light source having a light output control, a probe for delivering light to a volume, the probe being associated with one or more sensors, a light path operatively connected to the first light source, the light path providing light from the first light source to the probe. To avoid unsafe fluence levels incident upon the volume of interest in a clinical setting, the light output control may be set to an initial, relatively low value. After the light source is pulsed, the light output may be measured at or near the probe at the distal end of the light path. The measured light output can used to determine whether, and how much, to change the setting of the light output control.

3 Claims, 13 Drawing Sheets

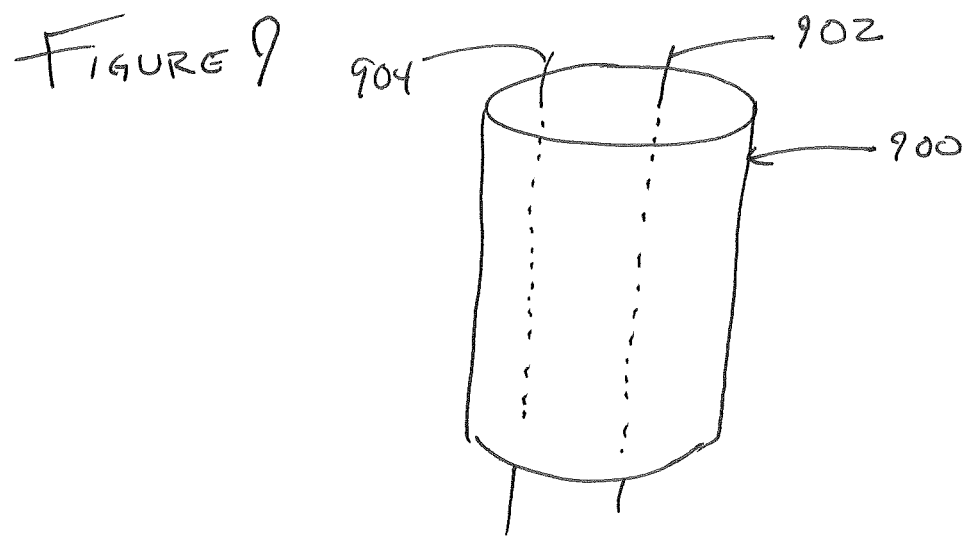

SYSTEM AND METHOD FOR ADJUSTING THE LIGHT OUTPUT OF AN OPTOACOUSTIC IMAGING SYSTEM

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of medical imaging, and in particular to system relating to optoacoustic imaging.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIG. 6b shows a side view diagrammatic representation of an effect of a ground glass beam expander on the light emitting from a fiber shown in FIG. 5a.

FIG. 6c shows a side view diagrammatic representation of an effect of a concave lens beam expander on the light emitting from a fiber shown in FIG. 5a.

FIG. 9 is a representation of another phantom with a variety of targets therein that may be used in connection with calibration and testing of an optoacoustic device.

FIGS. 10a-10c 2 show schematic orthogonal views of alternative embodiments of a probe that may be used in connection with the methods and other devices disclosed herein.

Figure 1:
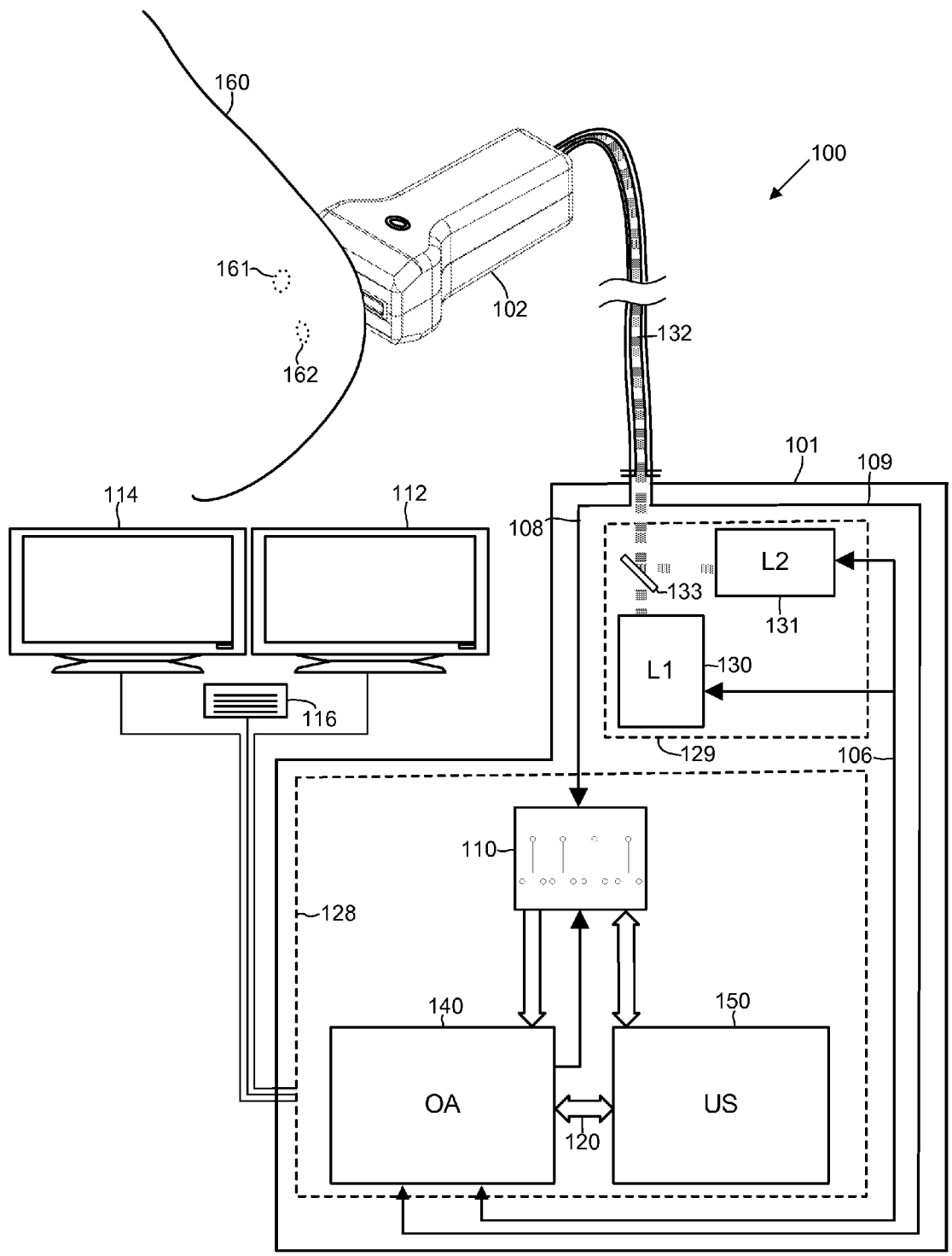
FIG. 1 shows a schematic block diagram illustrating an embodiment of a combined optoacoustic and ultrasound system that may be used as a platform for the methods and devices disclosed herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Reference will now be made in detail to various embodiments of the present invention, examples of which are illustrated in the accompanying drawings.

Generally, device 100 provides an optoacoustic system that may also be employed as multimodality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150.

The light system 129 is capable of producing pulses of light of at least two different wavelengths. In an embodiment, the light system 129 outputs should be capable of producing short pulses of light in each of those wavelengths, e.g., a pulse lasting less than about 100 ns, and more preferably around 5 ns. As will be apparent to one of ordinary skill in the art from this disclosure, the inventions disclosed herein may also be practiced using pulsed light comprising pulses lasting greater than 100 ns. In an embodiment, the light source 129 includes two separate lights 130, 131. The output of the light system 129 is delivered to the probe 102 via the optical path 132. In an embodiment, the lights 130, 131 are lasers producing light in the infrared, near-infrared, and/or visible spectrum. In an embodiment, light 130 and light 131 each produce light at a different wavelength in the infrared or near-infrared spectrum. In an embodiment, the optical path 132 used to deliver light from the light source 129 to the probe 102 is a fiber optic bundle comprising multiple strands of optical fiber. In an embodiment, the optical path 132 comprises sufficient optical fibers of sufficient size (diameter) to carry a short, high powered pulse of light to the distal end of the optical path 132. In an embodiment, the total pulse energy carried over the optical path 132 may be on the order of one or more millijoules. In an embodiment, the total energy per light pulse carried over the optical path 132 is less than about 100 millijoules. In an embodiment, the total energy per light pulse carried over the optical path 132 is in the range of about 10-30 millijoules, and the optical path 132 comprises around 1,000 optical fibers of about 150 microns each. In an embodiment, a single fiber can be used as the optical path. In such embodiment, the fiber may be 1000-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light system 129 may use Nd:YAG and Alexandrite lasers as its two lights 130, 131, although other types, and additional lights, may also be used. Lights 130, 131 should be capable of producing a short pulse of light, e.g., a pulse lasting less than about 100 ns, and more preferably around 5 ns. In an embodiment, the two lights 130, 131 can be separately triggered. In an embodiment, the light output by the lights 130, 131 may be projected onto the same light path 132 through the use of an optical element 133 that generally permits one light 130 to pass through from a first side to a second side, while reflecting one light 131 that strikes the second side. The use of optical element 133 or a similar element permits the alignment of the output of two lights 130, 131 such as lasers onto proximal end of the light path 132. In an embodiment, optical elements 133 can align the light output from more than two lasers, for example, through the use of multiple optical elements 133. In an embodiment, multiple light systems and light paths may be employed, with the light of each light system being carried on separate fibers that are intermingled at their distal ends. In an embodiment, optical elements 133 can consist of optical elements that are used to measure the light energy to determine energy per light pulse.

Although the total energy per light pulse carried over the optical path is in the order of tens of millijoules, because the pulse of lights 130, 131 is so short, the peak power output over the optical path 132 is frequently approaching or in the megawatt range. Accordingly, the output of lights 130, 131 has the capacity to cause the optical fibers and/or the cladding on the optical fibers to burn. Burnt optical fibers and burnt cladding can exacerbate the problem as they begin to transmit less light power and cause more heating. Accordingly, in an embodiment, sufficient number and size optical fibers are present in the optical path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the optical path 132 decreases. Moreover, when using more optical fibers, or optical fibers of a larger diameter, the output of light source 129 must be delivered to the optical path 132 across the wider diameter of the larger bundle. In an embodiment, regardless of the ultimate size of the proximal end of light path 132, the output of light source 129 should be distributed sufficiently across its cross section to prevent burn out failures when operating in expected peak power ranges.

In an embodiment, the fibers of the proximal end of the light path 132 may be fused to form a fused entry point to the optical path 132 for the output of light source 129. In an embodiment, the fiber ends can be fused by applying heat. Once the proximal end of optical path 132 has been fused, it will resist burnout at substantially higher peak power. For example, using a fused end light path 132 may permit carriage of three, four or even five times as much peak power. The ability to carry substantially higher peak power in a given optical path 132 permits use of a more flexible and lighter fiber optic bundle to carry the same peak power as an un-fused optical path 132. Thus, in an embodiment, where a ½" fiber optic bundle may have been required in an un-fused bundle of optical fibers forming an optical path, a ¼" fiber optic bundle with a fused proximal end may be used to carry the same peak power. A ¼" fiber optic bundle with a fused proximal end is approximately ¼ of the weight and much more flexible than a ½" fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, optical fiber of the type that may be used in light path 132 includes a transparent core surrounded by a transparent cladding material with a lower index of refraction. The core may be made from any transparent material, although excellent results have been observed using pure glass (i.e., silica). In an embodiment where a bundle of optical fibers are to be fused, the cladding may be removed in the area to be fused. In an embodiment, the cladding may be removed using a chemical process. For example, for some cladding, acetone may be used. The removal of cladding prior to fusing reduces the chance of particles of the cladding material becoming embedded in the fused end, as such particles may interfere with the light transmission across light path 132.

In an embodiment, the light output by the lights 130, 131 is sent towards a fused optical fiber bundle at the proximal end of light path 132 via an optical path, which may include optical element 133, internal to the light source 129. In an embodiment, light source 129 is a laser system capable of outputting laser light pulses, at one or a more wavelengths, onto light path 132. In an embodiment, light path 132 is a fiber optic bundle having a fused end proximal to the light source 129.

In an embodiment, the device 100 also comprises an electrical path 108 running to and/or from the probe 102 to the system chassis 101. In an embodiment, electrical path 108 runs to and/or from the probe 102 to a relay system 110 within the system chassis 101. The electrical path 108 may run near, alongside or coaxially with the optical path 132 from the probe 102 toward their respective connections on the system chassis 101. In an embodiment, the electrical path 108 comprises a plurality of separate coaxial wires. In an embodiment, the electrical path 108 is run in a common jacket with at least a portion of the optical path 132. Running electrical path 108 in a common jacket with at least a portion of the optical path 132 reduces the number of cables running from the system chassis 101 to the probe 102. Running electrical path 108 in a common jacket with at least a portion of the optical path 132 may minimize the diameter and weight of, and increase the durability of, the combined cables (i.e., optical path 132 and electrical path 108) running from the system chassis 101 to the probe 102.

In an embodiment, the plurality of coaxial wires is woven around at least a portion of the optical path 132. As discussed above, many considerations go into the number of separate optical fibers used in optical path 132. As discussed further below, numerous design considerations go into the number of separate electrical leads or traces forming the electrical path 108. In an embodiment, there are about 256 leads (corresponding to 256 transducers) forming the electrical path 108 and approximately 1,000 separate optical fibers forming the optical path 132, making the fiber:lead ratio about 4:1. As will be apparent, it is possible to comingle the optical fibers and leads or traces in the electrical path in a variety of ways, including, for example, bundling a group of individual fibers with a single electrical lead or trace, or bundling proportionally larger groupings of fibers and leads together. In an embodiment, the bundling of fibers and leads or traces would be done generally in the proportion of fibers:leads in the system.

One or more displays 112, 114, which may be touch screen displays, are provided for displaying images and all or portions of the device 100 user interface. One or more other user input devices (not shown) such as a keyboard, mouse and various other input devices (e.g., dials and switches) may be provided for receiving input from an operator. As an option, power and control signal lines 109 carry power to the probe 102 and control signals between the probe 102 and the computing subsystem 128.

In an embodiment, the connections between the probe 102 and the system chassis 101 may be formed into a flexible cable, which may consist of the light path 132, the control line(s) 109 and the electrical path 108. The flexible cable may be covered in a common outer jacket or sheath for convenience and ease of use. In an embodiment, a medial portion of the light path 132 forms the core of the single flexible cable, and medial portions of the electrical path 108 and/or control line(s) 109, if any, may be wrapped or braided about the medial portion of the light path 132. In an embodiment, a common outer jacket or sheathing encloses a fiber optic bundle forming a medial portion of the light path 132, a coaxial bundle forming a medial portion of the electrical path 108, and control line(s) 109, if any. In an embodiment, the fibers forming a medial portion of the light path, and the wires forming a medial portion of the electrical path 108, as well as control line(s) 109, if any, may be intertwined or intermingled with each other along the medial portion of the connections between the probe 102 and the system chassis 101.

In an embodiment, the distal end of the flexible cable(s) connecting the probe 102 and the system chassis 101 is associated with, and non-removably integrated as part of the probe 102. In an alternative embodiment, the distal end of the flexible cable(s) connecting the probe 102 and the system chassis 101 is removably associated with the probe 102. To removably associate the flexible cable(s) connecting the probe 102 and the system chassis 101 requires both optical fiber connection for the light path 102 and electrical connection for the electrical path 108 and control line(s) 109, if any.

In an embodiment, the light path 132 is split into two sections, and the two sections are brought together using an optical fiber connector in close proximity to the probe 102. The optical fiber connector may be physically located within the probe 102, or may span opening 404 (see FIG. 4), or be located outside the probe 102. In an embodiment, an optical fiber connector would mechanically couple and align the cores of the fibers making up the light path 132 so that light can pass from one section to the other without significant loss. In an embodiment, the facing ends of the two sections of the light path 132 are fused, and may be first stripped of cladding and then fused, to mitigate issues of core alignment. Regardless of whether the fiber ends are fused, the ends internal to light path 132 that are being connected by the optical fiber connector may be lapped and polished to improve light transmission. In an embodiment, probe 102 has a removable access panel that permits access to optical and/or electrical connectors located within the probe.

To removably associate the electrical path 108 and control line(s) 109, if any, removable electrical connectors are provided. In an embodiment, flex circuit is elongated so that connectors 314 which are connected to the end of electrical path 108 are accessible from a removable access panel, thereby permitting the disconnection of electrical path 108. In an embodiment, electrical path 108 (and control path 109, if any) is split into two sections, and the two sections are brought together using an electrical connector in close proximity to the probe 102. The electrical connector may be physically located within the probe 102, or may span opening 404 (see FIG. 4), or be located outside the probe 102. In an embodiment, an electrical connector would electrically couple the two portions of the electrical path 108 so that signals can pass from one section to the other without significant loss.

In an embodiment, the signals carried on the probe-side portion of electrical path 108 are analog signals, and are terminated into an analog-to-digital converter, and the signals carried on the other portion of the electrical path—the portion that connects to the system chassis 101—are digitized representations of the analog signals carried on the probe-side portion of the electrical path 108. In an embodiment, the signals carried on the electrical path 108 are digital signals given that the analog-to-digital conversion is performed in the body of the probe handle In an embodiment, the probe-side optical connector(s) and electrical connector(s) for the flexible cable(s) that operationally connects the system chassis 101 to the probe 102 are integrated into a single connector that can be operated to quickly disconnect the probe 102 from the cable.

Figure 2:
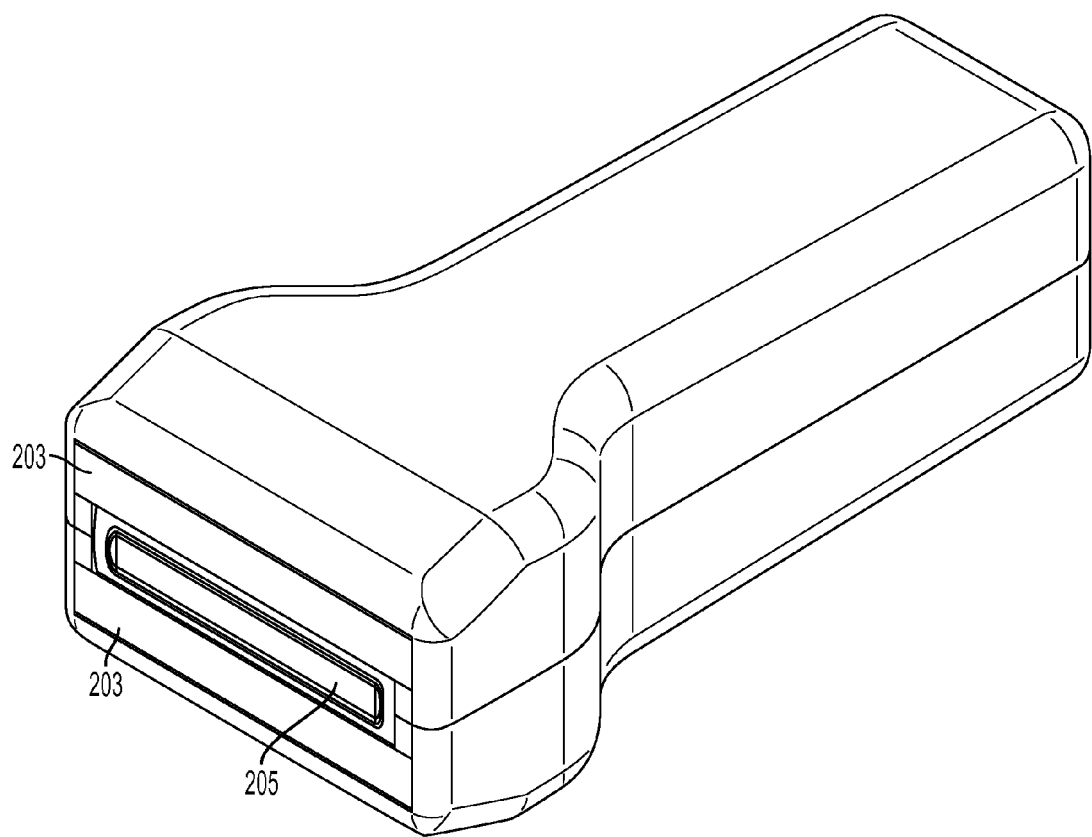
FIG. 2 shows a schematic orthogonal view of an embodiment of a probe that may be used in connection with the methods and other devices disclosed herein.

Turning now to FIG. 2, the probe 102 includes an array of ultrasound transducer elements forming an ultrasound transducer (not shown) covered by an acoustic lens 205. In an embodiment the ultrasound transducer comprises an array of piezoelectric elements that can both transmit and receive acoustic energy. In an embodiment, at least some of the ultrasound transducer elements are capable of detecting ultrasound frequencies over a wide range. For example, ultrasound transducer elements may be capable of detecting ultrasound in the range from about 50 KHz to 20 MHz. This range can be achieved by applying a high impedance load (e.g., in the range of 5,000 to 50,000 ohms) to achieve a lower frequency response. The ultrasound transducer elements are capable of generating electrical energy in response to receiving ultrasound acoustic energy. The electrical energy generated by the ultrasound transducer elements receiving ultrasound is transmitted to the computing subsystem 128 via electrical path 108.

The probe 102 also includes one or more optical windows 203 through which the light carried on optical path 132 can be transmitted to the surface of a three-dimensional volume 160. In an embodiment, it is desirable to locate one side of the optical window 203 as close as practical to the acoustic lens 205. The total area of an optical window 203 is important to maximize energy for a given fluence incident on the surface of the volume 160.

In an embodiment, the multiple strands of optical fiber making up the optical path 132 are terminated in two light bars (not shown). In an embodiment, the ultrasound transducer elements (not shown) are arranged in an array that runs along a geometric plane and are generally spaced equidistant from each other. In an embodiment, the light bars (not shown) are oriented longitudinally, on each side of the planar array of ultrasound transducer elements. Preferably the ultrasound transducer elements generate electrical energy in response to both ultrasound acoustic energy received in response to stimulation caused by the pulsed light sources 130, 131 (i.e., the optoacoustic return signal) and to ultrasound acoustic energy received in response to acoustic output of the ultrasound transducer elements.

Referring back to FIG. 1, in use, the probe 102 may be placed in close proximity with organic tissue, phantom or other three-dimensional volume 160 that may have one or more localized inhomogeneities 161, 162, such as e.g., a tumor, within. An ultrasound gel (not shown) or other material may be used to improve acoustic coupling between the probe 102 and the surface of the volume 160. The probe 102, when in proximity with the surface of the volume 160, can emit a pulse of a light through the optical windows 203 or an ultrasound through acoustic lens 205, and then generate electrical energy corresponding to ultrasound detected in response to the emitted light or sound.

In an embodiment, the computing subsystem 128 can trigger activity from light system 129 over control signal line 106. In an alternative embodiment, the light system 129 can create the trigger signal and inform the computing subsystem 128 of its activity over control signal line 106. Such information can be used to by the computing subsystem 128 to begin the data acquisition process. In this respect, it is noted that communication over control signal line 106 can flow both ways between the computing subsystem 128 (and/or the optoacoustic processing and overlay system 140 therein) and the light system 129.

In an embodiment, computing subsystem 128 can utilize control signal line 106 to control the start time and duration of light pulses from each light source 130, 131. The computing subsystem 128 can also trigger the probe 102 to emit ultrasound acoustic energy via the ultrasound transducer elements behind the acoustic lens 205.

In an embodiment, the computing subsystem 128 receives electrical signals representative of the ultrasound detected by the ultrasound transducer elements, in response to an ultrasound transmitted signal or an optically generated ultrasound signal, behind the acoustic lens 205 via electrical path 108. In an embodiment, the electrical signal representative of the ultrasound detected by the ultrasound transducer elements behind the acoustic lens 205 is the analog electrical signal created by the elements themselves. In such embodiment, the electrical signals representative of the ultrasound detected by the ultrasound transducer elements behind the acoustic lens 205 is transmitted to the computing subsystem via electrical path 108, and electrical path 108 is selectively directed by relay system 110 to the optoacoustic processing and overlay system 140 or the ultrasound instrument 150 for processing of the detected ultrasound. In such embodiment, the ultrasound instrument 150 can receive the same input (over the same connector) as it would receive from an ultrasound probe.

In another embodiment, the electrical signal representative of the ultrasound detected by the ultrasound transducer elements behind the acoustic lens 205 is digitized by an analog-to-digital converter which can be housed in the probe 102. In such embodiment, time-resolved electrical signal representative of the ultrasound detected by the ultrasound transducer elements behind the acoustic lens 205 is transmitted across the electrical path 108. Where the electrical signal is digitized at the probe 102, as will be apparent to one of skill in the art, the relay system 110 may be implemented to deliver digital data to the optoacoustic processing and overlay system 140 or the ultrasound instrument 150, or may not be needed at all.

The signal representative of the ultrasound detected by each of the plurality of ultrasound transducer elements behind the acoustic lens 205 may be carried on a separate wire over the electrical path 108. Alternatively, the signal representative of the ultrasound detected by a plurality of ultrasound transducer elements behind the acoustic lens 205, or even all of the ultrasound transducer elements behind the acoustic lens 205, may be multiplexed (e.g., time division or frequency division) utilizing a multiplexer in the probe and a demultiplexer in the computing subsystem 128.

In an embodiment, the ultrasound instrument 150 processes ultrasound-induced acoustic signals to produce ultrasound images and the optoacoustic processing and overlay system 140 processes light-induced acoustic signals to produce optoacoustic images. In an embodiment, the ultrasound instrument 150 and optoacoustic processing and overlay system 140 can be combined into an integrated system performing the combined functions of both. As discussed above, in an embodiment, electrical signals representative of ultrasound detected by the probe 102 and delivered to the computing subsystem 128 via electrical path 108 is switched between the ultrasound instrument 150 and the optoacoustic instrument 140 via relay system 110 in accordance with whether the signal results from ultrasound stimulation or light stimulation.

In an embodiment, tomographic images reflecting the ultrasound-stimulated data may be generated by the ultrasound instrument 150 and tomographic images reflecting the light-stimulated data may be generated by the optoacoustic processing and overlay system 140.

Images, including tomographic images, produced by the optoacoustic processing and overlay system 140 can be stored in a computer memory in that system, along with data associated with sequence or time and date of the image data that was captured. Images, including tomographic images, produced by the ultrasound instrument 150 may be transmitted to the optoacoustic processing and overlay system 140 via a suitable interface 170, where they can be stored, along with images generated from the light-stimulated data, in a time-synchronized manner. In an embodiment, images stored in the memory of the optoacoustic processing and overlay system 140 can be recorded to another memory, e.g., a non-volatile memory internal to, or external to, the device.

In an embodiment, the optoacoustic processing and overlay system 140 can overlay images produced by the ultrasound instrument with images produced by optoacoustic instrument 140 for storage in the memory and/or display on one or more monitors 112, 114. In an embodiment, the overlayed optoacoustic image may be shown in a distinct color to distinguish it from the ultrasound image. In an embodiment, the overlaid optoacoustic image may contain colors that correspond to details discernable through optoacoustic imaging, such as, for example, blood oxygenation. In an embodiment, oxygenated blood is shown more in red than blue, while deoxygenated blood is shown in more blue than red. As used herein, the expression overlaid includes merging of the image by mixing as well as traditional overlaying of the image.

In an embodiment, the device 100 may be configured to operate in a cycle comprising a sequence of successively generating and acquiring data relating to one of the device's modalities, i.e., ultrasound or optoacoustic. The minimum time spacing between operation of the device's modalities depends on the device 100 components and their ability to fully execute and recycle for use. In an embodiment, a user can select between a variety of preprogrammed cycles such as: ultrasound only; wavelength one only; wavelength two only; wavelength one and two; multiple iterations of wavelength one and two followed by ultrasound; and/or multiple iterations of ultrasound followed by wavelength one or two. Other combinations will be apparent to one of skill in the art. In an embodiment, additional cycles can be added by the machine operator. In an embodiment, the data collection of an entire cycle is generally intended to be directed to substantially the same portion of volume 160 and to be accomplished in rapid succession. In an embodiment, the device 100 cycles are normally in the range of 1 to 50 per second, and more typically in the range of 2 to 20 per second, as discussed above. The maximum cycle frequency is limited only by the capabilities of the cycle and modalities.

In an embodiment, the displays 112, 114 of device 100 can be configured to show various information depending upon the selected operating cycles. In an embodiment, any display 112, 144 or portion of the display can show at least one of the following: an ultrasound only image; a first wavelength response only image; a second wavelength response only image; a combined first and second wavelength response image; and/or an overlay ultrasound image and a wavelength response or combined wavelength response image. The combined first and second wavelength image may comprise a differential or other combinatorial means to provide the image. In an embodiment, an image can be displayed corresponding to each of the separate data collections in a cycle, or corresponding to the sum or difference between any or all of them.

In an embodiment, the device can be operated using a three-phase data collection operation, one phase generating and collecting data in response to ultrasound stimulus, one phase generating and collecting data in response to a first wavelength of light, and one phase generating and collecting data in response to a second wavelength of light.

Using proper wavelength(s), optoacoustics is effective in identifying blood within a volume 160, and using multiple wavelengths can be used to readily distinguish between oxygenated and deoxygenated blood. Similarly, using proper wavelengths, optoacoustics is effective for measuring localized hemoglobin content within a volume 160. Thus, for example, a malignant tumor, which is characterized by increased blood concentration and decreased oxygenation, will appear very differently in an optoacoustic image than a benign growth, which is not characterized by such an increased blood concentration and has more normal oxygenation. Moreover, specific wavelengths of light can be selected to better distinguish between various biological tissues and organs. While a large spectrum of infrared, near-infrared and visible wavelengths can produce optoacoustic response in biological entities, oxygenated blood is more optoacoustically responsive than deoxygenated blood to a light source having a wavelength of about 1064 nm, while deoxygenated blood is more optoacoustically responsive than oxygenated blood to a light source having a wavelength of 757 nm. The number and specific wavelength(s) of light used in the device 100 are selected in accordance with the makeup of the volume and the type of target that is of interest.

Figure 3:
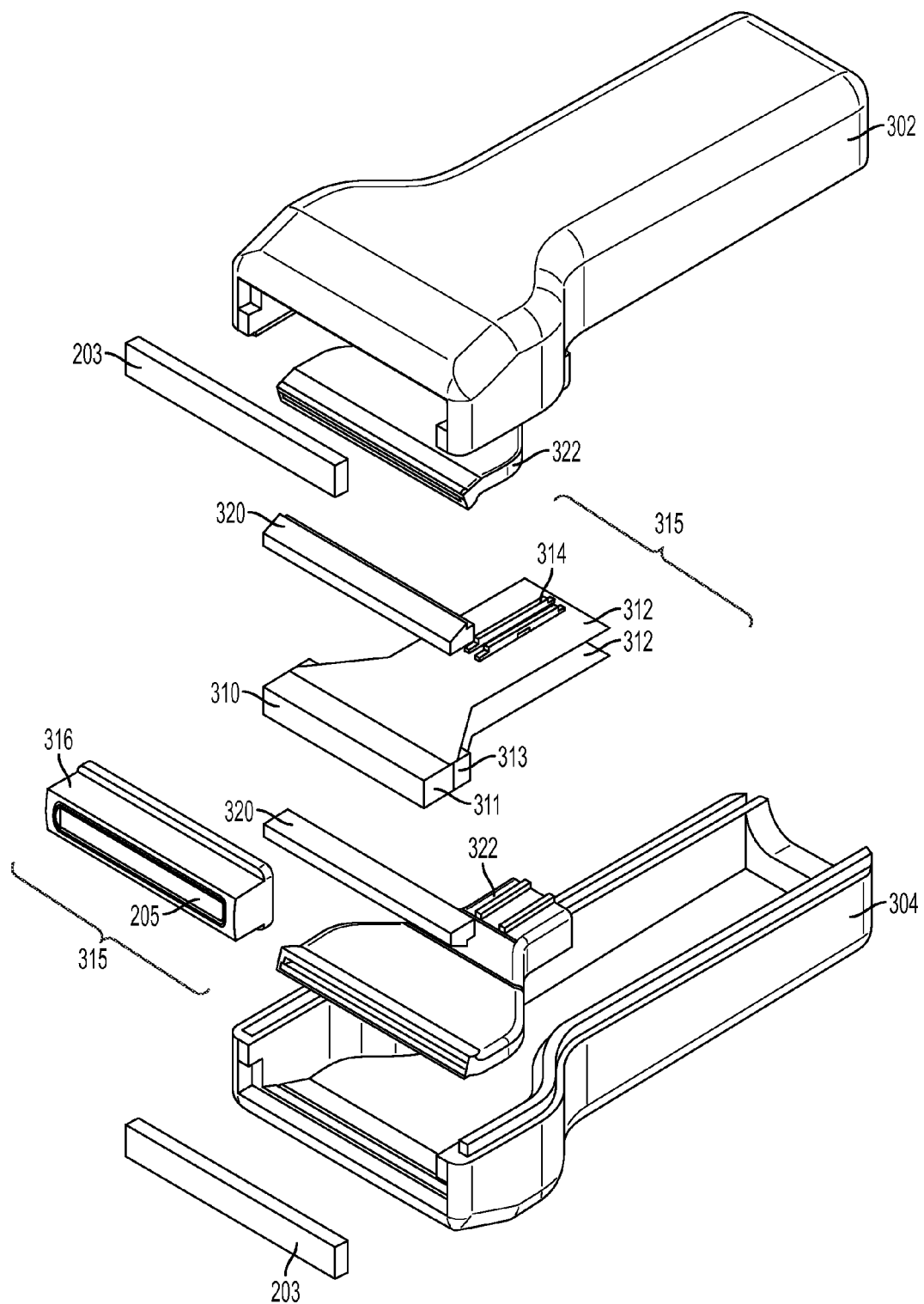
FIG. 3 shows an exploded view of an embodiment of the probe shown in FIG. 2.

FIG. 3 shows an exploded view of an embodiment of the probe 102 shown in FIG. 2. Shells 302, 304 are separated to show the components within the probe 102. The shells 302, 304 may be made from plastic or any other suitable material. The surfaces of the shells 302, 304 that may be exposed to light, and especially light generated by the light subsystem 129, are preferably both reflective (i.e., light colored) material and light scattering (i.e., having a scattering coefficient between 1 and 10). In an embodiment, the surfaces of the shells 302, 304 are highly reflective, i.e., more than 75% reflective. In an embodiment, the surfaces of the shells 302, 304 are very highly reflective, i.e., more than about 90% reflective. In an embodiment, the surfaces of the shells 302, 304 have low optical absorption, i.e., less than 25% absorptive. In an embodiment, the surfaces of the shells 302, 304 have very low optical absorption, i.e., less than about 10% absorptive. In addition, the material forming the shells 302, 304 should be acoustically absorbent to absorb, rather than reflect or transmit acoustic energy. In an embodiment, white plastic shells 302, 304 are used.

In an embodiment, flex circuit 312 comprises a plurality of electrical traces (not shown) connecting cable connectors 314 to an array of piezoelectric ultrasound transducer elements (not shown) forming ultrasound transducer 310. In an embodiment, flex circuit 312 is folded and wrapped around a backing 311, and may be secured thereto using a bonding agent such as silicon. In an embodiment, a block 313 is affixed to the backing 311 opposite the array of piezoelectric ultrasound transducer elements. In an embodiment, the ultrasound transducer 310 comprises at least 128 transducer elements, although it may be desirable to have a greater numbers of transducer elements, as additional elements may reduce distortion, and/or increase resolution, accuracy and/or depth of imaging of the device 100. The cable connectors 314 operatively connect the electrical traces, and thus, the ultrasound transducer 310, to the electrical path 108. In an embodiment, the electrical path 108 includes a coaxial wire for each ultrasound transducer element in the ultrasound transducer array 310.

The ultrasound transducer 310 fits within housing 316 so that the transducer elements are in close proximity to, or in contact with an acoustic lens 205. The acoustic lens 205 may comprise a silicon rubber, such as a room temperature vulcanization (RTV) silicon rubber. In an embodiment, the housing 316 and the acoustic lens 205 are formed as a single unit, from the same RTV silicon rubber material. In an embodiment, the ultrasound transducer 310, portions of the flex circuit 312, backing 311 and block 313 are secured within the housing 316 including an acoustic lens 205 using a suitable adhesive such as silicon to form a transducer assembly 315. The block 313 can be used to affix or secure the transducer assembly 315 to other components.

To whiten, and reduce the optoacoustic effect of light generated by the light subsystem 129 on an RTV silicon rubber acoustic lens 205 and/or the transducer assembly 315, in an embodiment, the RTV silicon rubber forming the acoustic lens 205 and/or the transducer assembly 315 may be doped with $TiO_2$. In an embodiment, the RTV silicon rubber forming the acoustic lens 205 and/or the transducer assembly 315 may be doped with approximately 4% $TiO_2$. In an embodiment, the outer surface of the acoustic lens 205 and/or the outer surface of the transducer assembly 315 may additionally be, or alternatively be, coated with a thin layer of metal such as brass, aluminum, copper or gold. Gold, however, has been found to have a tendency to flake or crack off of RTV silicon rubber. It has been found that the RTV silicon may be first coated with perylene, then coated with nickel, then coated with gold, and finally, again, coated with perylene. The multiple layering provides a durable gold coating without any substantial adverse effect to the acoustic properties of the acoustic lens 205, and without any substantial adverse effect to the transducer assembly 315 to detect ultrasound. In practice, it has been found that the perylene coatings beneath the nickel and over the gold layers, may curl at the edges rather than adhering well to the metals or rubber upon which it is deposited. Thus, as discussed in more detail below, in an embodiment, the portions of the acoustic lens 203 and/or transducer assembly 315 having a perylene coating edge are adapted to be mechanically secured against other components to prevent curling or peeling. In an embodiment, substantially the entire outer surface of the transducer assembly 315, including the acoustic lens 205, are coated with continuous layers of perylene, then nickel, then gold and then perylene again.

In an embodiment, a reflective material surrounds the transducer assembly 315 from the rear edge of the housing 316 to the end of the flex circuit 312 to reflect any light from the light path 132 that may be incident upon its surfaces. In an embodiment, an electromagnetic shield for RF energy surrounds the transducer assembly 315 from the rear edge of the housing 316 to the end of the flex circuit 312. In an embodiment, the lights 130, 131, may draw substantial energy (e.g., more than 1,000 volts for a few nanoseconds) creating substantial electromagnetic RF energy in the area of the probe 102. In an embodiment, the transducer assembly 315 from the rear edge of the housing 316 to the end of the flex circuit 312 is surrounded by a foil, which may act as a reflective material and an RF energy shield. In an embodiment, the foil is selected from the group: copper, gold, silver. In an embodiment, the foil is tied into the device's 100 electrical ground.

Spacers 320 space and position the light bar guide 322 with respect to the transducer assembly 315. Spacers are preferably made from materials that reduce its optoacoustic response to light generated by the light subsystem 129. In an embodiment, the spacers 320 are made from a material similar to the light contacting portions of the shells 302, 304. In an embodiment, the light bar guide 322 encases optical fibers that are part of the light path 132. In an embodiment, the optical fibers making up the light path 132 may be randomly (or pseudo-randomly) distributed throughout the light bar guide 322, thus making specific locations on the light receiving end of the fiber optic bundle at least pseudo-random with respect to corresponding specific locations on the light emitting end of the optical fibers retained by the light bar guide 322. As used herein the term randomly (or pseudo-randomly) distributed optical fibers making up the light path 132 means that the mapping of fibers from the proximal end to the distal end is done such that a localized interference in the light path 132 (e.g., burnout of a group of adjacent optical fibers) or a localized phenomenon (e.g., non-uniform light at the entry point to the optical path 132) will have an effect on the overall power transmitted, but will not have an operationally significant effect on any specific part of the distal end of the light path 132. Thus, two optical fibers adjacent at the proximal end are unlikely to be adjacent at the distal end of the optical path 132. Where optical fiber bundles are fused at the proximal and distal ends, the randomization must be done before at least one end is fused. As used herein the term randomly (or pseudo-randomly) distributed optical fibers does not mean that two different optical paths 132—i.e., for different devices 100—must differ from each other. In other words, a single "random" mapping may be reproduced in the light path of different devices 100 while still meeting the criteria of being a randomized. Because light generally behaves in a Gaussian manner, the entry point to the light path 132 is typically less than perfectly uniform. Randomization, as discussed above, may accommodate for the non-uniform entry of light into the light path 132. Randomization may also provide homogenization of light fluence over area illuminated, as it may aid in more evenly distributing the light fluence.

In an embodiment, the optical fibers encased by a light bar guide 322 all end on substantially the same geometric surface, e.g., a curved or flat plane. In one embodiment, after the fibers have been attached to the light bar guide 322, the fiber ends may be lapped and polished to provide for a more uniform angle of light emission. In an embodiment, the light bar guide 322, as installed in the assembled probe 102, directs the light emitting there-from at an angle slightly less than normal to the distal face of the probe 102, and specifically, at small angle inwards, towards the plane normal to and intersecting the center of the acoustic transducer array 310. In an embodiment, the distal end(s) of the optical path 132 should match—or closely approximate the shape of the acoustic transducer array 132.

The term bar, as used in "light bar guide" herein is not intended to import a specific shape. For example, the light bar guide 322 may guide the distal ends of optical fibers into substantially any shape such as, without limitation, a whole or part of a circle, oval, triangle, square, rectangle or any irregular shape.

In an embodiment, one or more light bar guides 322 and optical windows 203 are external to the shells 302, 304 housing the acoustic transducer assembly 315, and are adapted to be attached to the outer sides of one or more of the shells 302, 304.

In an embodiment, the angle of light emitting from the optical window 203 may be adjustable. In an embodiment, the light emitting from the optical window 203 may be adjustable across a range. At one end of the range, light may emit from the optical window 203 in a direction normal to the distal face of the probe 102, and at the other end of the range light may emit from the optical window 203 at an inward angle of up to 45 degrees or more towards the plane normal to and intersecting the center of the acoustic transducer array 310. The range can be smaller or larger.

In an embodiment wherein a probe has two optical windows 203, the angle of light emitting from both optical windows 203 can be adjustable, individually, or together. Where adjusting the angle of light emitting from both optical windows 203 together, the light direction would, in each case increase or decrease the angle of inward projection, that is, projection towards the plane normal to and intersecting the center of the acoustic transducer array 310. In this manner, a larger light fluence can be directed deeper into the volume 160 (by angling toward normal), or shallower (by angling more inwardly).

Controlling the direction of the light angle can be done by moving the light guide 322, or it can be accomplished optically through the use of post-light path 132 optics. Optical solutions may include the use of one or more lenses and/or prisms to re-direct the light that has been transmitted through the light path 132. Re-directed light can be directed to illuminate a desired area, such as an area directly beneath the transducer elements 310. Controlling the direction of light transmitted by the probe 102 is useful to maintain safe and optimize the direction of the light with respect to the skin and the transducers.

Control line 109 may be used to send commands redirecting light and/or to report the actual direction of light at the time a light pulse is emitted from the light path 132. The angle of the light emitting from the optical window 203 may be important data to consider when interpreting acoustic information resulting from the light pulse.

In an embodiment, the device 100 can adjust the angle of incident laser light emitting from the probe 102. Adjustment of the angle of incident laser light emitting from the probe 102 may be carried out under the control of commands which may be sent via control line 109, or may be manually carried out. In an embodiment, a standoff may be used, e.g., to help direct incident laser light to the desired depth, or closer to the surface than can be achieved without a standoff. In an embodiment, the standoff is relatively transparent to both acoustic and light, and preferably to acoustics in the ultrasound range and light one or more of the wavelengths utilized by the light source 129. While the use of standoffs is known in ultrasound applications to aid in imaging of objects close to the surface of the volume 160 because ultrasound resolution lacks the capability to detect objects at a nominal distance from its transducers, the use of a standoff in the present application is for a different purpose, namely, to allow the light sources to be aimed directly under the transducer elements 310. In an embodiment, the standoff is separate from the probe 102, and placed between the volume 160, and the distal end of the probe 102 comprising the acoustic lens 205 and one or more optical windows 203. In an embodiment, the standoff may be integral to the probe, and may be move into place and withdrawn as desired.

Optical windows 203 may also be part of the probe 102 assembly. In an embodiment, the optical windows 203 is spaced from the end of the light bar guide 322, and thus, from the ends of the optical fibers making up the light path 132. The term optical window, as used here, is not limited to mechanically or optically flat optical matter, or solely to transparent optical matter. Instead, the term is used to refer to an optical element that may or may not effect light passing therethrough, but will permit at least a substantial portion of the light incident on the side of the window proximal to the light path 132 to exit the probe assembly 102 in a manner that is dependent on the properties of the optical element. In an embodiment, the optical window 203 may be transparent, which permits transmission of light, and specifically light emitted from the end of the light path 132, to volume 160 when the distal end of the probe 102 is in contact with or close proximity to that volume 160. In an embodiment, the optical window 203 may be translucent, permitting diffusion and transmission of light, and specifically light emitted from the end of the light path 132, to volume 160 when the distal end of the probe 102 is in contact with or close proximity to that volume 160. In an embodiment, the optical window 203 may be a lens, permitting the shaping and directing of light, and specifically light emitted from the end of the light path 132, to volume 160 when the distal end of the probe 102 is in contact with or close proximity to that volume 160.

In the assembled probe 102, one edge of the optical window 203 is in close proximity to, or in contact with, the transducer assembly 315. The proximity of the optical window 203 to the transducer assembly 315 allows light emitted from the optical window 203 to be emitted from a location close to the acoustic lens 205, and thus close to the plane of the transducer array 310.

In use, a coupling agent (e.g., gel) may be used to improve the acoustic contact between the distal end of probe 102 and the volume 160. If the coupling agent makes contact with the distal end of the optical fibers forming the light path 132, extraneous acoustic signal may be generated in response to light transmission over the light path 132. In an embodiment, the distal end of the probe 102, including optical window 203, mitigates the potential acoustic effect of a coupling agent in response to light emitting from the light path 132 by creating a gap between the coupling agent and the distal end of the optical fibers.

Figure 4:
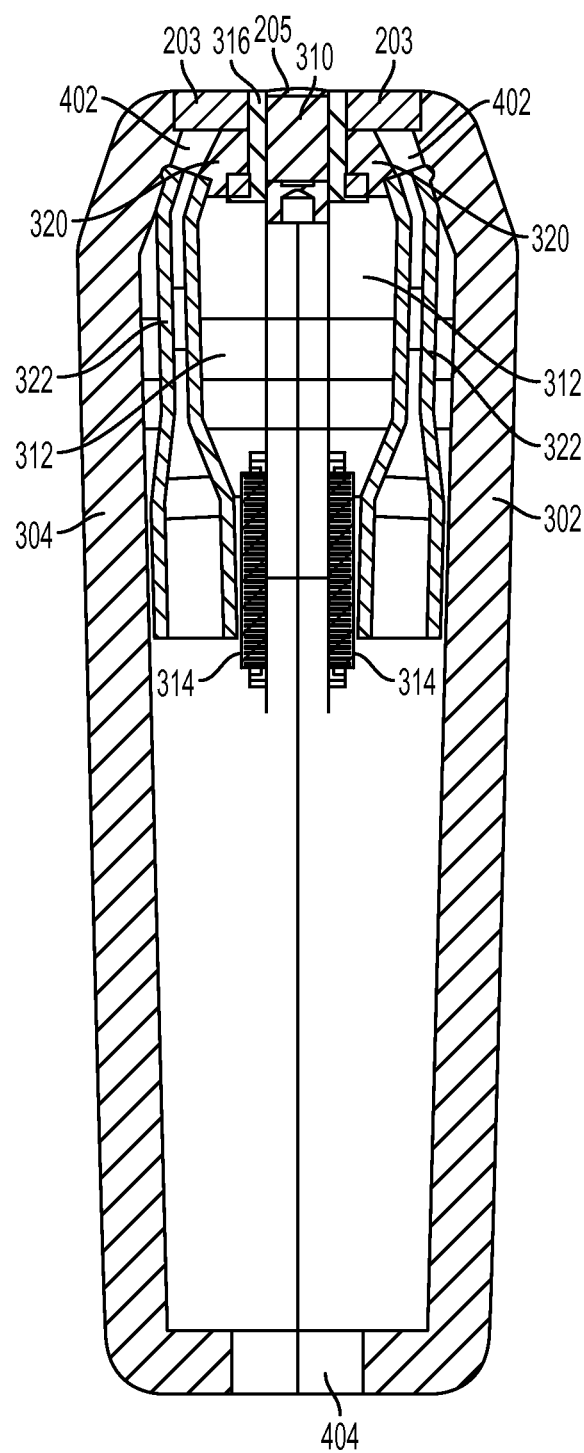
FIG. 4 shows a cutaway view taken along the centerline of the wider side of the probe shown in FIG. 2.

FIG. 4 shows a cutaway view taken along the centerline of the wider face of one embodiment of an assembled probe 102 such as the probe shown in FIG. 2. Shells 302, 304 support optical windows 203 and transducer assembly 315 at the distal end of the probe 102. Spacers 320 supported by transducer assembly 315 and shells 302, 304 aid in the positioning of optical windows 203 and light bar guides 322, and in maintaining gap 402 between light bar guides 322 and the optical windows 203.

The distal ends of the optical fibers making up the light path 132 may be positioned such that they do not create a physical sound conduction path to the volume 160 or to the acoustic transducers 310. In an embodiment, the gap 402 serves the purpose of preventing high frequency sound conduction path between the distal ends of the optical fibers making up the light path 132 and the volume 160 or the acoustic transducers 310. Specially selected materials, as discussed below, can be used to ensure that the light bar guide 322 reduces and/or minimizes the physical sound conduction path between the distal end of the light path 132 and the volume 160 or the acoustic transducers 310.

Flex circuit 312, with piezoelectric transducer elements (not shown) thereon, wraps around backing 311, and electrically connects the piezoelectric transducer elements with the cable connectors 314 at each end of the flex circuit.

Opening 404 in the shells 302, 304 provides an opening for optical path 132 (FIG. 1), electrical path 108 (FIG. 1) and optional power and control lines 109 (FIG. 1) to enter the inside of the probe 102. In an embodiment, a rubber grommet (not shown) may be used to provide stability and strain relief to the paths or lines passing into the probe 102 through opening 404.

Figure 5A:
FIG. 5a is a side view not-to scale diagrammatic two dimensional representation of light exiting an optical fiber.
Figure 5B:
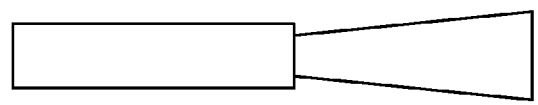
FIG. 5b shows an end view of a light pattern that may result on a surface from placement of optical fibers directly on to that surface.

Turning to FIG. 5a, a typical pattern of light striking a surface in close proximity to the ends of ten optical fibers is shown. Today, typical, reasonably flexible optical fibers have a diameter in the range of about 50 to 200 microns. Light exiting an optical fiber tends to expand slowly, see, for example, an illustrative example of light expanding after leaving the end of an optical fiber in FIG. 5b. The rate of expansion of the light beam leaving an optical fiber is a function of the diameter of the optical fiber and the refraction index of the optical fiber material. When a group of optical fibers are placed in close proximity to a surface to be illuminated, a light pattern like that seen in FIG. 5a results.

In an embodiment, optical fibers having smaller diameters are employed to broaden the illuminated area and minimize weight and increase flexibility of the light path 132. Light diverges as it exits a fiber optic, and its divergence as it exits is inversely related to the diameter of the fiber—in other words, light diverges faster out of smaller diameter fiber optics. Thus, for example, optical fibers in the range of under 50 microns, and potentially less than 30 microns may be desirable to broaden the illuminated area, thus reducing, or potentially eliminating the need for a beam expander. In an embodiment, the distal end of one or more groups of the optical fibers comprising the light path 132 may be fused to avoid the characteristic pattern of light shown in FIG. 5a.

In an embodiment, an optoacoustic probe should produce a relatively uniform light distribution incident upon the surface of the illuminated volume. It may also be desirable for an optoacoustic probe to produce a relatively large area of light distribution. Providing a relatively large and uniform light distribution permits an optoacoustic probe to deliver a maximum amount of energy without exceeding a specific light fluence on any given area of the illuminated surface, which can maximize patient safety and/or improve the signal-to-noise ratio. For these reasons, it is not desirable to locate the optical fiber ends in too close proximity with the surface of the illuminated volume, and thus, obtain a small or uneven light distribution such as the one seen in FIG. 5a.

In an embodiment, the optical fibers may be moved away from the surface of a volume to be illuminated. Moving the end of the optical fibers away from the surface of the volume to be illuminated will cause the beams emitted from each optical fiber to expand, and produce a more uniform area of light distribution. One potential issue associated with moving the optical fibers away from the surface of the volume to be illuminated, is the optoacoustic effects caused by stray portions of the expanding beam. Another potential issue is the effect of enlarging the distance (between the end of the optical fibers and the surface to be illuminated) on the shape or size of a probe. Further, increasing the number of optical fibers (and thus enlarging the area of the fiber bundle emitting light) will increase the cost, weight and flexibility of the optical path 132 (FIG. 1), and may also affect the size of the probe.

Because the probe 102 is designed to be handheld, it is desirable to keep the probe head (the wider, distal portion of the probe 102) short so that the probe stem (the narrower, proximal portion of the probe 102) is relatively close to the surface of volume 160. Additionally, because the probe 102 is designed to be handheld, its total thickness is also a consideration for comfort, convenience and operational effectiveness. Accordingly, locating the distal ends of the fibers forming light path 132 at a sufficient distance from the optical window 203 to permit expansion to fill the optical windows 203 with uniform light fluence is not preferred. Similarly, using a very large number of fibers to enlarge the area of the fiber bundle held by the light bar guide 322 at the distal end of the light path 132 and thereby attempting to permit expansion to fill the optical windows 203 with uniform light fluence is also not preferred as it would, among other things cause undue weight, inflexibility, size and cost. Moreover, reducing the size of the optical window 203 would reduce the total potential safe energy output of the device, and thus, is not preferred.

Figure 6A:
FIG. 6a shows an end view of a desirable light pattern for use in connection with the optoacoustic techniques discussed herein.
Figure 6B:
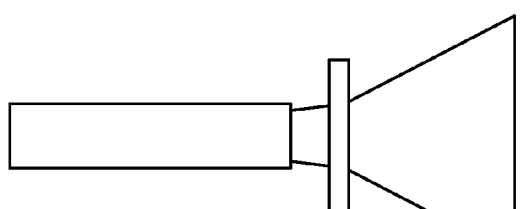
Figure 6C:
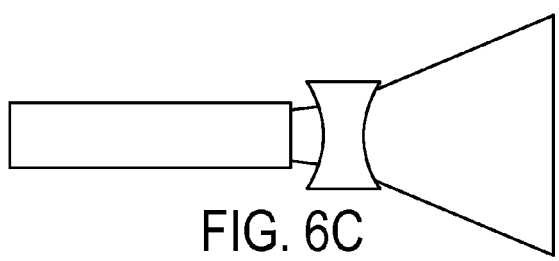

Turning to FIGS. 6b and 6c, in an embodiment, a beam expander 601b, 601c may be used to expand the beam of light, causing it to become more uniform over a shorter distance. FIG. 6b shows the use of a ground or frosted glass beam expander 601b, while FIG. 6c shows the use of a lens beam expander 601c. In an embodiment, where the light bar guide 322 is generally rectangular, a lens beam expander 601c may be a cylindrical convex lens or a cylindrical concave lens. In an embodiment, a convex lens (not shown) may be used as a beam expander. It will be apparent to one of skill in the art that other lenses, lens systems or other optical systems or combinations thereof, can be used to spread and more evenly distribute the light.

Referring back to FIG. 4, in an embodiment, the light bar guides 322 are angled inward toward the ultrasonic imaging plane on the end retaining the distal ends of the fibers. The inward angling of the distal end of the light bar guide 322 permits the light emitting there-from to better fill, and thus, evenly illuminate the optical window 203. Gap 402, which may include a beam expander, may provide space for the light transmitted across the light path 132 to expand to fill the optical window 203. The inward angling tends to cause the direction of the light incident on the surface of the volume 160 to strike the surface at an angle less than normal, and thus, potentially, to better propagate into the volume beneath the acoustic lens 205 covering the ultrasound transducers 310.

Turning back to FIG. 1, because the probe 102 is intended for handheld use, the weight and flexibility of the light path 132, the electrical path 108 and the optional power and control lines 109 is of consideration. In an embodiment, to make the light path 132 lighter and more flexible, the light path 132 is constructed from as few fibers as possible. A limiting factor to how few a number of fibers that can be used, is the amount of light carried across the optical path 132. The transmission of too much light over a fiber will damage the fiber. The light path 132 must carry the total amount of light that will be fluent on the surface of the volume 160, plus any light lost (e.g., absorbed or scattered) between the light source 129 and the surface of the volume 160 illuminated. Since the maximum area of illumination is known not to exceed the size of the optical window 203, and because the area of illumination is subject to fluence limits per unit area, a total light energy carried by the light path 132 can be approximated by multiplying the fluence limit by the size of the optical windows 203. The FDA provides numbers for the human safe level of fluence.

The volume 160 illuminated generally has its own optoacoustic response, which is especially apparent where light fluence is greatest, namely, at the surface of the volume 160. Increasing the area of illumination onto the surface of the volume 160 (e.g., by increasing the size of the optical window 203 and beam) reduces the optoacoustic affect generated by the surface of the volume 160 itself, and thus may reduce the undesirable optoacoustic signal generated by the surface of the volume 160 itself as compared to a desired signal representing the inhomogenities 161, 162.

In addition to unwanted optoacoustic signal generated by the surface of the volume 160 itself, there may be other sources of unwanted optoacoustic signals that can be detected by the ultrasound transducer, such as the side walls surrounding the space between the optical windows 205 and the respective light bar guides 322, the acoustic lens 205 and portions of the transducer housing 316. The optical windows 203 and any optional beam expander 601b, 601c may also be sources of unwanted optoacoustic signals that can be detected by the ultrasound transducer.

In an embodiment, the walls surrounding the space between the optical windows 205 and the respective light bar guides 322 may be made from a material that has high acoustic absorption properties and/or that is white and/or has high light scattering and/or reflecting properties. Using materials having these characteristics may reduce unwanted optoacoustic signals that can be detected by the ultrasound transducer. In an embodiment, the spacers 322 can be made from a resin material such as Micro-Mark CR-600, a two part high performance casting resin that dries to a white color.

In an embodiment, a layer (not shown) of material that has high acoustic absorption properties and/or that is white and/or has high light scattering properties is placed between the transducer assembly 315 and the light bar guides 322 in the assembled probe 102. Alternatively, the layer may be applied directly to the transducer assembly 315 or the light bar guide 322 where the two parts contact in the assembled probe 102. This layer may reduce unwanted optoacoustic signals that can be detected by the ultrasound transducer. In an embodiment, the layer can be made from a resin material such as Micro-Mark CR-600, a two part high performance casting resin that dries to a white color. In an embodiment, the layer (not shown) may also comprise a reflective coating. In an embodiment a reflective coating of gold is applied to the layer to reflect light that might otherwise strike the layer.

In an embodiment, anti-reflective coatings may be used to reduce the optoacoustic signature of the optical window 203 and/or the beam expander 601b, 601c. In an embodiment, magnesium fluoride may be used as an anti-reflective coating on the optical window 203 and/or the beam expander 601b, 601c. Anti-reflective coatings may be used to reduce and/or minimize energy absorbed or reflected by the optical window 203.

In an embodiment, the optoacoustic signature of the transducer assembly 315 and/or acoustic lens 205 can be reduced by whitening. In an embodiment, an acoustic lens 205 comprising RTV silicon rubber may be whitened and have its optoacoustic signature reduced by being doped with about 4% $TiO_2$. It is believed that the $TiO_2$ doping increases the reflectivity of the acoustic lens and therefore the absorption, and also has a scattering effect that tends to diffuse the optoacoustic response of the RTV silicon rubber, bringing the response down to a lower frequency which can be more easily filtered. As discussed above, the outer surface of the transducer assembly 315 and/or acoustic lens 205 may be given a metal coating, such as gold, copper, aluminum or brass. In an embodiment, the metal coating, and in particular, gold, reduces the optoacoustic signature of the transducer assembly 315 and/or acoustic lens 205. It is believed that gold reduces the optoacoustic signature of the acoustic lens 205 because of its high reflectivity in the light spectrum.

As discussed above, the optical fibers at the end of the optical path 132 are retained by the light bar guide 322 with all of the fiber ends retained by the light bar guide 322 located on substantially the same plane. In an embodiment, the fiber ends may be fixed in place using mechanical force, an adhesive, or a combination of mechanical force and an adhesive. The fibers may be glued near their distal end to keep them in the desired location and pattern, and/or to reduce output of mechanical energy due to laser firing. In an embodiment, the spaces between optical fibers fixed within the light bar guide 322 may be filled with a material having one or more of the following characteristics: sound absorbing, light scattering, white and/or light reflecting. In an embodiment, the optical fibers, which may be encased by a light bar guide 322 at the distal end of the light path 132 are fused. Fusing fibers at the distal end of the light path 132 may permit the light emitting from the light path to be more uniform.

In an embodiment, a reflective coating is placed on areas of the shells 302, 304 where laser light emanating from the optical path 132 may strike it, including with the assembled probe, and in the areas designed to make skin contact, e.g., near the optical window 203 and other portions of the distal end of the probe 102. In an embodiment, the shells 302, 304 are coated in gold where laser light emanating from the optical path 132 may, or is likely to strike it. In an embodiment, portions of the shell 302, 304 may be made from gold, although at present this may be cost prohibitive.

In an embodiment, a proximity detector system (not shown) is used to determine that the distal end of the probe 102 is on or very near the surface of a volume. Among the reasons such a proximity detector system is desirable is that it can be used to prevent pulsing of the light source 129 when the probe 102 is not in close proximity to a volume 160 under inspection, or to be inspected. This may be a safety issue as the light source 129 may produce light at levels that can be harmful, e.g., to the eyes. The proximity detector system may be implemented in the form of: a mechanical contact switch at the distal end of the probe; an optical switch looking at reflections of a non-harmful beam from the surface of the volume 160; a conductive switch that is closed by contact with the volume 160 and/or any acoustic gel or other materials between the volume 160 and the distal end of the probe; a conductive switch and a standoff comprising a conductive surface for contact with the distal end of the probe 102; a conductive switch and a thin, optically and acoustically transparent, conductive surface applied to the surface of the volume 160 of interest; an acoustic transducer switch that can detect close proximity of the volume 160 by transmitting and looking for the reflection of a sound within a specific time; an acoustic transducer switch that can detect close proximity of the volume 160 by using a narrow shape sound transmitter and receiver and using the reflection to detect proximity; using one or more of the transducers in the transducer array as a proximity detector by looking for a signal return; or by operating the device 100 in an ultrasound mode and looking for an ultrasound image.

In an embodiment, an optical detector (not shown) may be located in the probe 102 to take a measurement from which output energy can be estimated or deduced. In an embodiment, the optical detector will measure reflected energy such as energy reflected by the beam expander or optical window. In an embodiment, the optical detector will measure scattered energy such as energy scattered by the materials surrounding the gap 402. The measurement of the optical detector can be transmitted to the system chassis 101 via control signal line 109, where it can be analyzed to deduce or estimate the light output of the probe 102. In an embodiment, control functionality in the system chassis 101 can control or regulate the light output of the light system 129, and thus the light output of the probe 102 based on a measurement made by the optical detector. In an embodiment, control functionality in the system chassis 101 can control or regulate the gain in the transducer receivers to compensate for variation of the light output of the probe 102 based on a measurement made by the optical detector. In an embodiment, the computing subsystem 128 can trigger differing activity from light system 129 over control signal line 106 based on a measurement made by the optical detector. In an embodiment, a measurement made by the optical detector can be used to control for variations in the electrical system or the power to the device 101. Similarly, in an embodiment, a measurement made by the optical detector can be used to control for variations in the optical path 132 or other optical elements of the device 100. In an embodiment, the optical detector can be used to cause the fluence of light output by the probe 102 to remain close to, but below, safe limits by accommodating for variations in electrical or optical characteristics that might otherwise cause the fluence of light output by the probe 102 to exceed or fall far below the safe limit.

In an embodiment, a safety feature would prevent disconnection of the probe 102 from the flexible cable when the system is in operation (e.g. when the laser is firing). To implement this safety feature, in an embodiment, the system 100 can use control line(s) 109 to operate a mechanical lock on the connector between the probe and the flexible connector. In an embodiment, a fail-secure mechanical lock would only permit disconnection of the probe 102 from the flexible cable when a specific control line(s) 109 was at voltage greater than a prespecified amount.

As discussed above, the device 100 comprises a probe 102 that, in an embodiment, is capable of transmitting both ultrasound and light to a volume 160, and is capable of receiving and processing an ultrasonic response to the transmitted ultrasound and light. The ultrasonic response to the transmitted ultrasound is typically in the range of about 2 to 8 MHz centered on 5 MHz, while the ultrasonic response to transmitted light is typically in a much broader range, such as the range of about 50 KHz to 20 MHz or more, typically centered in the range of 6 MHz to 8 MHz. In an embodiment, ultrasound is transmitted and received by the transducers 310, while light is transmitted by a light 130, 131, across the optical path 132, and across the optical window 203 or other aperture, the ultrasonic response thereto is received by separate transducers (not shown) tuned to receive the higher frequency range typically generated by the optoacoustic effect. The separate transducers are operated with high impedance amplifiers, e.g., having an impedance of more than 200 ohms, and preferably being about 500 ohms or more. Where the ultrasound is received by separate transducers from the optoacoustic response, the signals representing ultrasound response may be carried back to the system chassis 101 on separate wires of the electrical path 108 from the signals representing optoacoustic response.

In an embodiment, ultrasound is transmitted by the transducers 310, and the ultrasonic response thereto is received by the transducers 310, and light is transmitted by a light 130, 131, across the optical path 132, and out the optical window 203, and the ultrasonic response thereto is also received by the transducers 310. In such embodiment, the transducers 310 are operated with high impedance amplifiers having an impedance of more than 1K ohm and less than about 100K ohms, and more preferably between 2K and 10K ohms input impedance. In an illustrative embodiment, the transducers 310 may be operated with a 5K ohms input impedance amplifier.

In an embodiment where the probe 102 is equipped with ultrasound transducers 310 and separate transducers (not shown) tuned to receive the higher (vs. broader) frequency range typically generated by the optoacoustic effect, the optoacoustic response for light that transmitted by a light 130, 131, across the optical path 132, and out the optical window 203, may be received by both the transducers 310 and by the separate transducers. Using both sets of transducers to receive ultrasound responsive to the optoacoustic effect may capture additional data that can be used to better analyze target 161, 162 within a volume 160.

Figure 7:
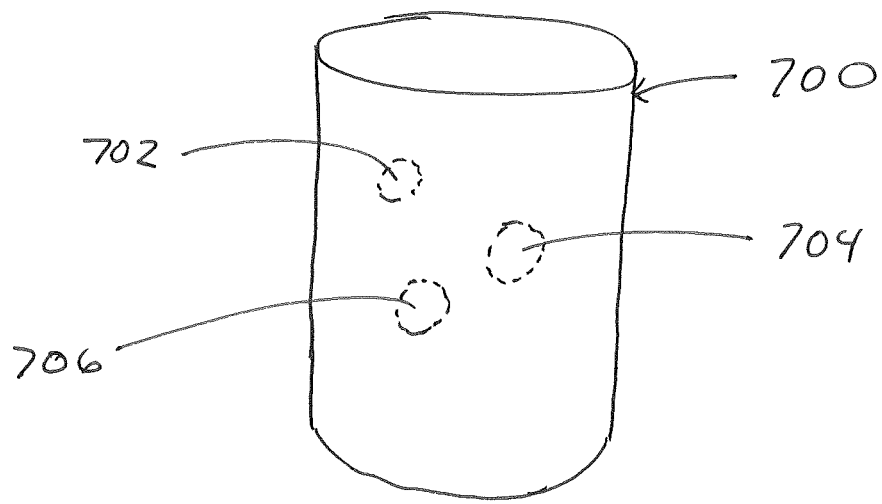
FIG. 7 is a representation of a phantom with a variety of targets therein that may be used in connection with calibration and testing of an optoacoustic device.
Figure 8:
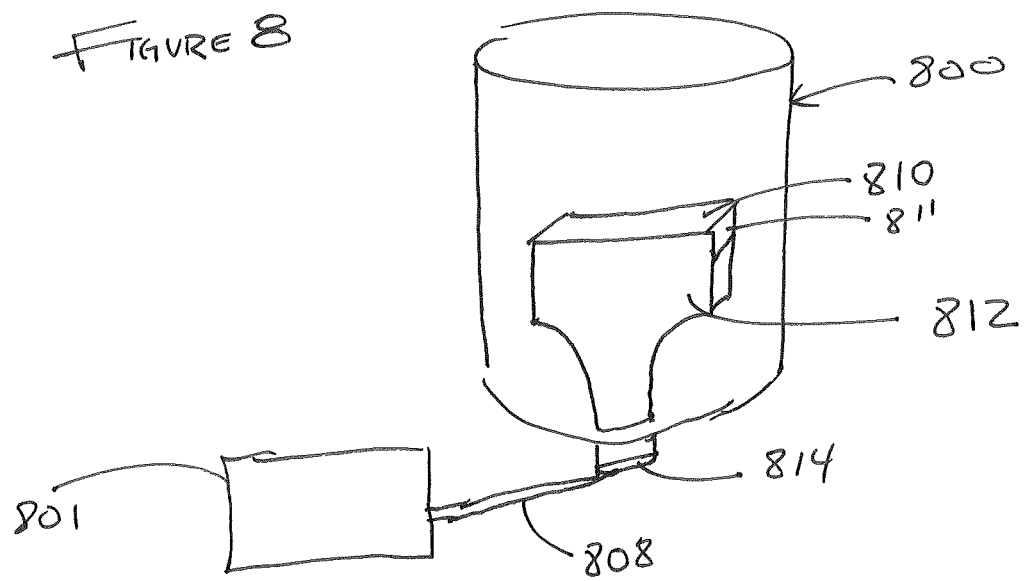
FIG. 8 is a representation of an active phantom that may be used in connection with calibration and testing of an optoacoustic device.

Turning to FIGS. 7-9, phantoms formed from plastisol are useful for registration and calibration. FIG. 7 shows a phantom 700 for use in connection with an optoacoustic imaging device and/or a multimodal ultrasound and optoacoustic imaging device. The phantom 700 comprises several targets 702, 704 706. In an embodiment, the targets 702, 704 706 are dissimilar, one being particularly responsive to a first stimuli but not a second, one being particularly responsive to a second stimuli but not the first, and one being particularly responsive to both the first and second stimuli. In an embodiment, the first stimuli may be an optoacoustic pulse at a first wavelength and the second stimuli may be an optoacoustic pulse at a second wavelength. In an embodiment, the first stimuli may be a traditional ultrasound signal and the second stimuli may be an optoacoustic pulse at one or more wavelengths. To make materials responsive to the various stimuli, doping is generally used. For optoacoustic response, material is doped with an absorber at the relevant frequency or frequencies. For ultrasound response, material is doped to be denser. Using phantom 700 the response to the first or second stimuli can be demonstrated and or calibrated in response to the degree to which 702, 704, and/or 706 targets are doped. This allows the determination of the doping percentages at which it is difficult to differentiate between target responses.

FIG. 9 shows a phantom 900 for use in connection with an optoacoustic imaging device and/or a multimodal ultrasound and optoacoustic imaging device. The phantom 900 comprises several targets 902, 904 embedded in plastisol. In an embodiment, the targets 902, 904 are generally linear and similar. In an embodiment, the targets 902, 904 are natural or synthetic horsehair. Using phantom 900 multiple modalities such as optoacoustics and ultrasound can be co-registered. In an embodiment, a multimodality probe is coupled to the phantom, and an image showing the output of each modality is presented on the screen overlaid upon one another. Using a joystick or other input device, an operator can manually co-register the images, thus providing co-registration for the multimodality probe. In an embodiment, the images of each of the modalities are compared by a computer, and automatically co-registered.

FIG. 8 shows an active phantom 800 for use in connection with an optoacoustic imaging device and/or a multimodal ultrasound and optoacoustic imaging device. The phantom 800 comprises an active target 812 embedded in plastisol and target control 801. In an embodiment, active target 812 comprises a linear array of transducers 810 on a backing 811; the transducers 810 are operatively connected to target control 801 through the body of the active target 812, connector 814 and by electrical path 808. Target control 801 can create signals that drive the transducers 810. In an embodiment, target control 801 selectively creates signals to output a known ultrasound pattern and/or simulates an optoacoustic return signal. Using phantom 800 permits testing and calibration of the optoacoustic return signal receiving and processing portions of an optoacoustic device 100 without concern for the integrity of the light output system.

Figure 10A:
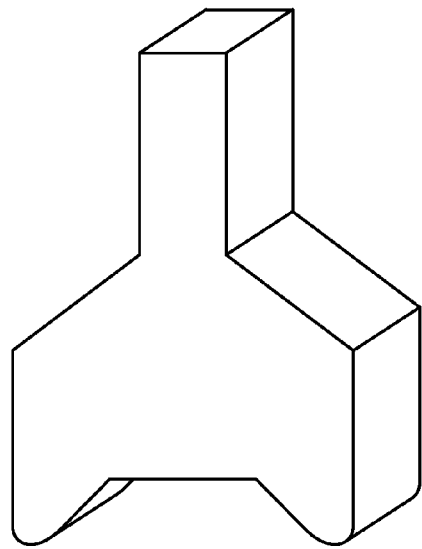
Figure 10B:
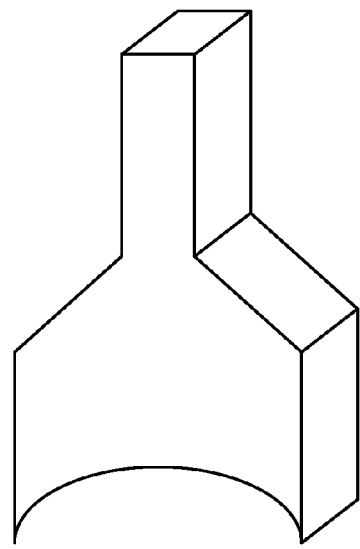
Figure 10C:
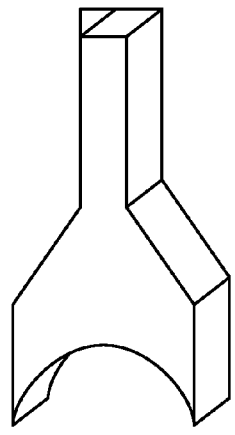
Figure 11A:
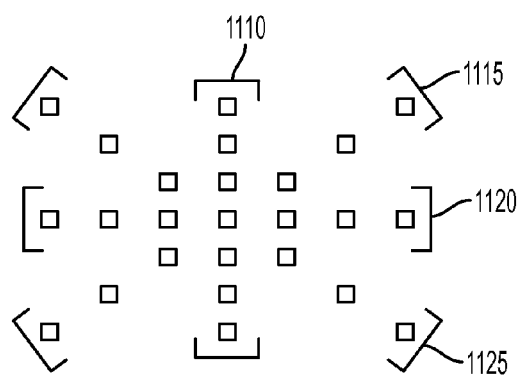
FIGS. 11a-11c show a representation of several examples of various organizations of two dimensional arrays of transducer elements.
Figure 11B:
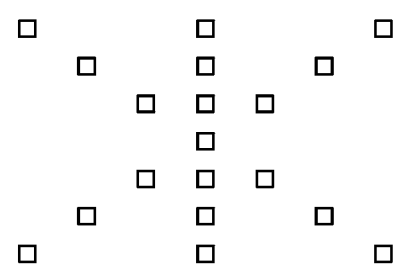
Figure 11C:

As discussed above and shown in the Figures discussed above, the probe 102 may have a linear array of transducers 310 that are adapted to receive the optoacoustic return signal through an acoustic lens 205. Other transducer geometries are also desirable. Turning to FIGS. 10a-c, in various embodiments, a linear transducer array may be oriented with sides that protrude at angles from the plane of the central portion of the array, or may be in the general shape of an ellipse or a semi-circle. Turning to FIGS. 11a-c, in various embodiments, a transducer array may be provided in a two dimensional shape as generally illustrated. Although the illustrations show only small numbers of transducers, e.g., 7 per line, in practice, many more transducers would be used. As discussed above, in an embodiment, 128 or more transducers per line, may be used. For example, in FIG. 11a, an illustrative array is shown comprising four generally linear arrays of transducers aligned on simple Cartesian coordinates in asterisk-type configuration ands sharing a common center transducer. In FIG. 11b, an illustrative array is shown comprising three generally linear arrays of transducers wherein the transducers are arranged similarly distant from one another on concentric rings in the various arrays, and also arranged in asterisk-type configuration and sharing a common center transducer. In FIG. 11c, an illustrative array is shown comprising three generally linear arrays of transducers arranged in a simple grid.

With respect to each of numerous geometries shown, to develop an image from the optoacoustic return signal requires (i) that the transducers are coupled to the volume 160 containing the target(s) of interest when used to detect an optoacoustic return signal, and (ii) that the detected optoacoustic return signal is processed using information relating the relative position of the transducers to each other in space. Transducers may be use in a flexible array that adapts to the shape of the volume 160 when coupled therewith, provided that the relative position of the transducers to each other in space is known, and used in processing the optoacoustic return signal.

In an embodiment, an optoacoustic probe can be used to detect the optoacoustic return signal by sampling the transducers for a period of time after the optoacoustic inducement, such as a laser, has been deployed. In an embodiment, at least some of the desired content of the optoacoustic return signal is in the frequency range of about 6 MHz to 8 MHz. Thus the optoacoustic return signal may be sampled at 30 MHz, which is a sufficient sampling rate for at least some of the desired content of the signal. In an embodiment, the sampling apparatus is capable of sampling up to 256 channels 65 MHz. Thus, where an optoacoustic probe has 128 or 256 transducers, these may be sampled at the 30 MHz rate.

In an embodiment, an optoacoustic probe can detect the optoacoustic return signal by sweeping through multiple transducer elements or through multiple groups of transducer elements. For example turning to FIG. 11a, the 25 shown illustrated transducer elements are shown in four groups 1110, 1115, 1120, 1125 of seven, noting that each group shares a common center element. In an embodiment, after an optoacoustic pulse such as from a laser, a first cycle of the detection of the optoacoustic return signal can be conducted first through one group 1110, then a second group 1115, then a third group 1120, and then a fourth group 1125. Once that first cycle of the detection of the optoacoustic return signal is complete, a second cycle, a third cycle and so on may continue. The sampling apparatus discussed in an embodiment above capable of sampling up to 256 channels 65 MHz is also capable of sampling two separate arrays of 256 transducers at 30 MHz, or four arrays of 128 transducers at 30 MHz. Accordingly, in an embodiment as shown in FIGS. 11a-c, a sampling apparatus may be used to sweep through two or more groups of overlapping (e.g., FIGS. 11a-b) or unique (e.g., FIG. 11c) transducers and thus sample the optoacoustic return signal in response to a single optoacoustic event, such as the firing of a single laser pulse.

As will be apparent to one of skill in the art, sampling apparatus are capable of sampling at rates higher than the illustrative one discussed above. Using sampling apparatus that can sample more channels or at faster rates would permit a larger number of total samples to be generated in response to a single optoacoustic event. Accordingly, it is within the scope of this specification and the inventions disclosed herein, to use larger groups, and/or more groups, of transducers than are illustrated above, to be swept through in response to a single optoacoustic event.

Advantages exist in connection with each of the differing transducer geometries discussed above. The straight linear array is compact, cost efficient, easily handled, and is the most commonly used in standard ultrasound B-mode imaging. The curved or winged linear arrays may conform better to the irradiated volume, and thus, provide better coupling. The non-linear (multiple row, also known as 1.5 dimensional) arrays permit additional angles from which to resolve the optical return signal from a given voxel, which may improve resolution and/or add clarity and contrast to the image and/or may better support three-dimensional imaging applications. Flexible arrays may also provide better coupling with the volume. The non-linear arrays can allow transducer elements that are optimized for ultrasound to co-exist with transducer elements that are optimized for optoacoustics within the same probe. Different transducer elements are used to create either the US or OA images.

An optoacoustic return signal can be generally acquired within a window of 100 microseconds for depths of about 4 centimeters. In an embodiment, the frequency of light events is anticipated to be generally on the order of every 50 to 100 milliseconds (0.0005 to 0.001 seconds). Accordingly, the data acquisition occurs less than 1% of the time, and closer to between 0.5% or 0.1% of the time, leaving more than 99% of the time where no data acquisition is occurring. Electrical noise may be created by powering the light subsystem 129 and/or other components of the system 100. Accordingly, in an embodiment, to prevent electrical noise from affecting the data acquisition, a synchronization is utilized to prevent powering unnecessary components during that period, leaving power only to the preamps, analog-to-digital converters and multiplexer. In an embodiment, the synchronization between power and data acquisition allows for the power system to be optimally electrically quiet during the acquisition time period. In an embodiment, this may be achieved by powering down noisy digital components during this period or allowing charged capacitors to power the acquisition hardware at this time. In an embodiment, this is triggered by the same trigger that starts the acquisition cycle and is controlled by the master processor to control the turning on/off of the peripheral components not involved with the acquisition cycle. In an embodiment, this takes from a few nanoseconds to a few microseconds.

As discussed above, in an embodiment, the same transducers are used to receive acoustic-generated ultrasound and to receive the optoacoustic return signal. The geometry of acoustic-generated ultrasound transducers is not optimal for receiving the optoacoustic return signal. Accordingly, in an embodiment, separate transducers are used for the acoustic-generated ultrasound and the optoacoustic return signal. The acoustic-generated ultrasound transducers can have a narrower band because the transducer itself sends the signal that it needs to detect. The optoacoustic return signal transducer can have a wider band, such as, for example, 50 KHz to 20 MHz. This wider band is preferred, among other reasons, because gain falls faster with depth on the optoacoustic return signal. Thus, in an embodiment, a plurality of transducers is used to receive the acoustic-generated ultrasound and a separate plurality of transducers is used to receive the optoacoustic return signal. In an embodiment the plurality of transducers used to receive the acoustic-generated ultrasound and the separate plurality of transducers used to receive the optoacoustic return signal comprise approximately the same number of transducers. In an embodiment the plurality of transducers used to receive the acoustic-generated ultrasound and the separate plurality of transducers used to receive the optoacoustic return signal each comprise at least 128 transducers, and more preferably, would comprise at least 192 transducers. In an embodiment the plurality of transducers used to receive the acoustic-generated ultrasound and the separate plurality of transducers used to receive the optoacoustic return signal each comprise at least 256 transducers. In an embodiment, the transducers used to receive the optoacoustic return signal have a wider band frequency response than separate transducers used to receive the acoustic-generated ultrasound. In such an embodiment, the transducers used to receive the optoacoustic return signal have a frequency response from at least about 1 MHz to 5 MHz, and more preferably, from about 100 KHz to about 10 MHz, and even more preferably from about 50 KHz to about 20 Mhz. In such an embodiment, the transducers used to receive the optoacoustic return signal may use high impedance amplifiers, such as 100 KΩ or more, and more preferably, 500 KΩ or more. In such an embodiment, the transducers used to receive the acoustic-generate ultrasound would use amplifiers having an impedance of less than 1 KΩ, and more preferably about 200Ω. The use of separate transducers would eliminate the need for relay system 110, and the switching of the transducer outputs thereby between the optoacoustic processing and overlay system 140 and the ultrasound instrument 150.

As discussed above, in an embodiment, the same transducers are used to receive acoustic-generated ultrasound and to receive the optoacoustic return signal. Where the same transducers are used to receive acoustic-generated ultrasound and to receive the optoacoustic return signal, amplifiers should be used that have an impedance within the range of about 1-10 KΩ, and more preferably amplifiers should be used that have an impedance of approximately 5 KΩ.

In an embodiment, the sampling of an optoacoustic return signal is performed in a variable manner, where the gain of the amplifiers associated with each of the sampled channels is adjusted over time, and is hereinafter referred to as time gain compensation or TGC. TGC ramps up gain on the acoustic input as the optoacoustic return signal becomes fainter, thus more accurately sampling the signal, and providing more normalized collected data and maintaining good signal-to-noise ratio as the signal become fainter. Optoacoustic return signal becomes fainter with time for several reasons, including that the later optoacoustic return signals have generally traveled further. Thus, generally optoacoustic return signal becomes fainter as the depth of a target increases. However, the magnitude (and thus needed gain) of optoacoustic return signals are also affected by the location and source of illumination. Generally, less light penetrates to deeper depths, and thus, the optoacoustic return signals are fainter because an optoacoustic event occurring at the surface of a volume generally induces a smaller response at a deeper depth. TGC is utilized to compensate for the later, fainter optoacoustic return signals.

The optoacoustic device 100 may comprise sensors (not shown) that can measure power and from that infer both total and peak power of the light subsystem 129, and performance and efficiency of the optical path 132. In an embodiment, sensors such as photo detectors can be placed within or in close proximity to the light subsystem 129 and within or in close proximity to the probe 102. In each case, the sensors would take a measurement during the illumination of a light 130, 131 which can be used to infer total and peak power. For this purpose, one or more sensors can be placed inside the probe 102 to measure reflection from the optical window. Similarly, one or more sensors can be placed within the light subsystem 129 to measure light reflected therein. Deviation over time in the measurements inferred between the two sensor locations may be indicative of anomalies in the light path 132.

Discussing now an embodiment of the system having sensors (not shown) such as photo detectors within or in close proximity to the probe 102. In an embodiment, one or more sensors may be placed within the probe, in the gap 402 to measure reflection from the optical window. Alternatively, or additionally, in an embodiment, one or more sensors may be provided light directly from a component of the light path 132, such as from one or a small plurality of the optical fibers that make up the light path 132. Alternatively, or additionally, in an embodiment, one or more sensors may be provided light by another path provided within the probe. Thus, for example, one or more sensors could be located within the end of the probe opposite the optical windows 203, and an auxiliary light path (not shown) can e.g., carry light directly from the light path 132 or reflected from the optical window or otherwise, to the one or more sensors. Alternatively, or additionally, in an embodiment, one or more sensors may be arranged to detect light originating in the light path 132 after it has been reflected from the surface of three-dimensional volume 160. Using information from sensors arranged to detect light reflected from the surface of three-dimensional volume 160, in combination with information concerning the light transmitted through the optical window 203 towards the volume 160 (such as information from sensors measuring output from the light subsystem 129 or from the optical window 203), can provide diagnostic information concerning the volume 160. Such diagnostic information may include the absorptiveness, or the darkness, of the volume 160.

In an embodiment, the foregoing sensors can be tuned to specific wavelengths through the use of an optical filter. Thus, for example, sensors within or in close proximity to the probe 102, sensors within or in close proximity to the light subsystem 129, sensors receiving light from an auxiliary light path and/or sensors arranged to detect light reflected from the surface of the volume 160, can be filtered to discriminate between the wavelengths of light produced by the light subsystem 129 and/or any extraneous light. Accordingly, sensors may be provided to detect (or potentially to reject) specific light frequencies, such as the light from one of the two light sources 130, 131.

In an embodiment, one or more sensors within or in close proximity to the probe 102 can be used as part of a triggering system and method for starting detection optoacoustic return signal data. In such a triggering system or method the detection of a specific threshold value of light by the one or more sensors can send a detection control signal to the computing subsystem 128. In an embodiment, the detection control signal is sent over the power and control signal lines 109 to the optoacoustic processing and overlay system 140. The detection control signal is used by the computing subsystem 128 to initiate (after any appropriate delay, if any) the process of obtaining the optoacoustic return signal data, for example, by "sampling" data from the ultrasound transducer elements. As discussed above, because the one or more sensors can be optically filtered to detect specific light frequencies, the detection control signal may be specific to one or more frequencies of light, and may initiate differing sampling rates, or delays, based upon the different frequency of light.

In an embodiment, one or more sensors within or in close proximity to the probe 102 can be used as part of a system and method for safely starting the optoacoustic system 100 and then bringing the laser to its safe power potential. Although laser light sources (e.g., 130, 131) generally have a controllable power output, many factors can affect the total power output by a light source regardless of its setting. Ambient temperature, for example, may affect the power output by a laser. Similarly, fluctuations in electrical power can also affect the power output by a laser. In addition, the light path 132 can negatively affect the light output of laser light sources (e.g., 130, 131). Fibers within the light path 132 can burn out, or lose transmissive properties as they age or are used. Moreover, fibers that are positioned in a bend can lose transmissive properties. Thus, the setting of a light source (e.g., 130, 131) to a particular output level is not necessarily determinative of the light that reaches the other end of the light path 132, and ultimately, the volume 160. Accordingly, in an embodiment, the light source (e.g., 130, 131) is set to a relatively low power. The relatively low power should be selected to be a power that, in the event everything is functioning at its peak output or transmissiveness, would not exceed a desired maximum fluence on the volume 160. Once the light source (e.g., 130, 131) is pulsed, a measurement from the one or more sensors is used to infer the fluence of light delivered to the volume 160. In the event that this inferred fluence is lower than the desired fluence level (or a desired range of fluence levels), the output from the light source can be increased, and the process repeated. Likewise, in the event that the inferred light fluence is higher than a desired maximum, the output from the light source can be decreased. Because the system 100 is capable of a significant number of laser events per second, the rate of increase to the light output, and thus, the potential increase in the fluence level between laser events, can be kept relatively small. In an embodiment, the amount of change in output from the light source may be larger when the inferred fluence is farther away from the desired fluence level (or a desired range of fluence levels), and smaller when the inferred fluence is closer to the desired fluence level.

In addition to providing a method for safely starting the optoacoustic system and bringing the laser to its safe power potential, the same process can be run as a closed loop control to ensure that the laser fluence is being monitored and controlled, and that to the extent it exceeds a predefined threshold such coming within some margin of a safety limit, its output power can be lowered. Similarly, operating the process as a closed loop control can also ensure that the laser output is being set to a maximum desirable setting even as the operating conditions of the system 100 (e.g., ambient temperature and electrical power) change, and regardless of the existing or changing condition of the light path 132. Keeping the laser at or close to its highest safe level permits the largest light fluence, and thus, strongest optical return signal. In an embodiment, one or more of the following: the target fluence level, the acceptable hysteresis around the target fluence level and a maximum fluence level, are user selectable, and when selected can be used by the processing running as a closed loop control to maintained the laser as specified. The closed loop control process can be used to normalize pulse-to-pulse power output.

In an embodiment, where the measurement taken at the one or more probe-proximate sensors falls below a predetermined threshold for a given laser output, as a failsafe, the lasers may be shut down. Such a level may reflect a failure or detachment of the light path 132, or other unsafe condition.

In an embodiment having one or more sensors within or in close proximity to the probe 102 and one or more sensors within or in close proximity to the light subsystem 129, the sensors can be utilized as part of a system for and method to detect faults in the light path 132 or to provide a safety control for faults in the light path. In an embodiment, the light output of the light subsystem 129 would be expected to be proportional to the light output of the light path 132 and the light fluence exiting the optical windows 203. The use of one or more light subsystem-proximate sensors can permit detection of differences in the expected amount of the light incident on the several sensors. As discussed above, the light path 132 can negatively affect the light output by of laser light sources (e.g., 130, 131). For example, the light path 132 can be negatively affected by burn out, old or broken fibers within the bundle. Thus, setting a light source (e.g., 130, 131) to a particular output level is not necessarily determinative of the light that reaches the other end of the light path 132, and ultimately, the volume 160. By employing both one or more light subsystem-proximate sensors and one or more probe-proximate sensors, performance of the light path 132 can be detected and monitored.

In an embodiment, the one or more light subsystem-proximate sensors are used to measure the power of the light entering the light path 132 and one or more probe-proximate sensors are used to measure the power of the light that has been transmitted through the light path 132. The measurement taken at the one or more light subsystem-proximate sensors may be used to predict a measurement at the one or more probe-proximate sensors. In an embodiment, deviation from the predicted measurement at the one or more probe-proximate sensors can be used to identify potential problems with the light path 132. In an embodiment, the sensor readings are recorded with other data concerning the event. In an embodiment, deviations are assessed to determine whether action needs to be taken, for example, whether the user needs to check the light path 132 connections, or whether the light path 132 is in need of maintenance (e.g., straightening, cleaning, lapping and polishing or other maintenance) or even replacement. In an embodiment, where the measurement taken at the one or more probe-proximate sensors deviates from its predicted measurement by more than a predetermined amount, as a failsafe, the lasers may be shut down. Such a deviation may represent a failure or detachment of the light path 132 or other fault or unsafe condition.

In an embodiment having one or more sensors within or in close proximity to the probe 102 and/or one or more sensors within or in close proximity to the light subsystem 129, the measurements from the sensors, along with the other settings of the machine (including the commanded light output) should be stored with the data other data associated with the light pulse, such as the optoacoustic return signal.

In an embodiment, a calibration phantom comprising one or more embedded photosensitive sensors is provided. As with the above-described sensors, the sensors in the phantom can be used to infer total and peak power, as well as light distribution. Deviation over time in the measurements inferred between the phantom sensors and the other sensors may similarly be indicative of anomalies. Moreover, changes over time between the readings of the various sensors within the phantom or within the probe may be indicative of issues with the evenness of light output of the probe. The use of such sensors rather than the system transducers avoids acoustic involvement, thus eliminating error introduced by the transducers themselves.

In an embodiment, a second calibration phantom may be provided with acoustic targets rather than sensors. The use of such a phantom eliminates any error that may be introduced by the sensors themselves. Calibration using both the acoustic target and sensor phantoms would provide a cross-check and mitigate the potential for calibration error. Time gain compensation must be properly calibrated.

Figure 12:
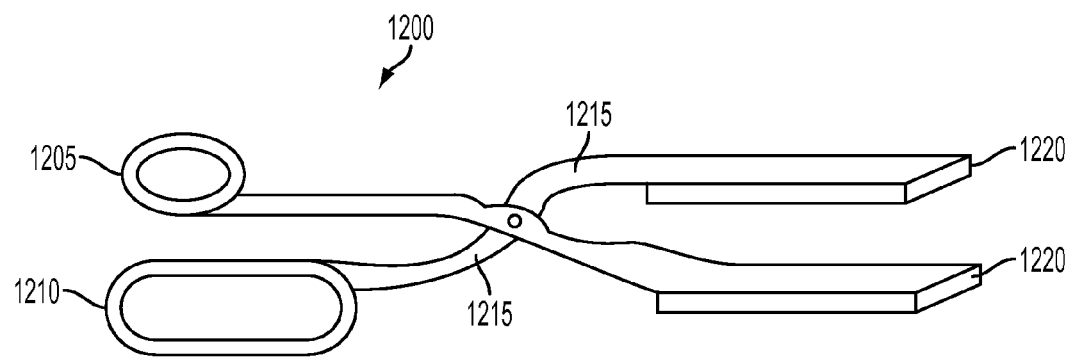
FIG. 12 is an illustrative example of a two-armed forceps-like probe having transducer arrays on its arms which can be physically positioned using finger grips.

In yet a further embodiment, linear or non-linear arrays may be physically separated from each other, but the data there-from may be recovered in response to the same optoacoustic event. Turning to FIG. 12, as an illustrative example, a two (or more)-armed forceps-like probe 1200 may contain linear or non-linear transducer arrays 1220 extending from arms 1215 that can be physically positioned using finger grips 1205, 1210 at the time of use, for example, on each side of a volume to be irradiated. In another example (not shown), two or more of the fingers of a glove could contain linear or non-linear arrays of transducers which can be manually positioned. In each case, although preferable, it is not necessary to know the orientation of one array with respect to the other in use. And while it is necessary that the optoacoustic event irradiate the volume sufficiently to permit the at least a portion of the transducer arrays coupled to the volume to detect an optoacoustic return signal, it is not necessary that the optoacoustic event is generated from the probe.

Figure 13:
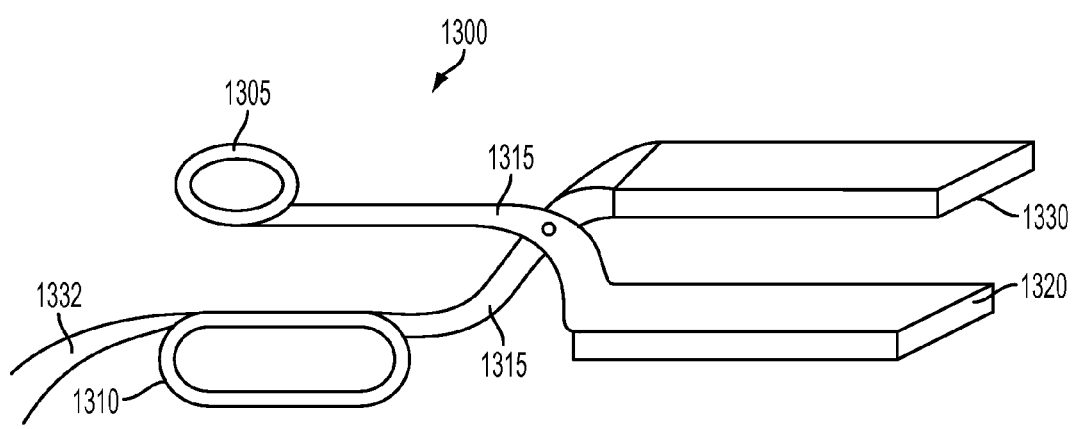
FIG. 13 is an illustrative example of a two-armed forceps-like probe having a transducer array on one arm and a light source on the other for use in forward transmission mode.

Turning to FIG. 13, a forceps-like probe 1300 for use in generating an optoacoustic image by acquiring data in a forward transmission mode is shown. The probe 1300 may contain a linear or non-linear transducer array 1320 situated across from an optical window 1330 that can project light output from a suitable light source such as a laser. The separation of the optical window from the transducer array mitigates numerous sources of noise that interfere with the sampling process of the optoacoustic return signal.

Each transducer in probe 102 may exhibit slight variations in operation. Accordingly, in an embodiment, once completed, probe 102 is tested in connection with one or more known test subjects such phantoms (see FIGS. 7-9) and the probe's measured response from the test subject is recorded. In an embodiment, the test subjects will produce a known optoacoustic return signal, either in response to a known optoacoustic event, or, by active control of the phantom. Variation from the known/expected optoacoustic return signal can be identified, and associated with each specific channel (e.g., transducer) comprising the variation. In this manner, the probe's own response characteristics—to the extent they may differ from probe to probe—can be accounted for, and may be normalized in later processing. Thus, if a particular transducer produces a signal that differs from the expected signal, that difference can be accounted for, and then later normalized.

In an embodiment, information associated with a probe's own response characteristics may be stored within the probe itself, and can be reported to the optoacoustic processing and overlay system 140 via power and control signal lines 109. In an alternative embodiment, information associated with a probe's own response characteristics may be stored outside the probe, and can associated with a serial number or other identifier of the probe. The optoacoustic processing and overlay system 140 can obtain the probe response characteristics after identifying the probe for use. In an embodiment, the probe response characteristics may be stored in an network accessible location, either on a local disk, network, or on the Internet, and are made accessible to the optoacoustic processing and overlay system 140 via a connection (not shown) to that disk, network or the Internet. In an embodiment, the optoacoustic processing and overlay system 140 would obtain a unique identifier from the probe, and would thereafter query a database on the local device, network, or over the Internet, to obtain response characteristics for the probe associated with the unique identifier. Probe response characteristics may be recorded and stored at or near the time the probe is manufactured. In an embodiment, probe response characteristics may be updated by running a specialized test on the probe—the test having a known/expected response.

The probe identifier may be obtained by the optoacoustic processing and overlay system 140 after machine startup, but before engaging the light output. In an embodiment, the probe identifier is recorded on a bar code on the probe, and the bar code is scanned prior to the device causing light output. In an embodiment, the probe identifier is recorded on a computer-readable memory in the probe, and is queried by, or reported to the optoacoustic processing and overlay system 140 after startup, but prior to engaging the light output.

Because the probe identifier is known, the device can maintain statistics of probe usage. For example, in an embodiment, the device may maintain statistics of the operation of the probe in optoacoustic mode, including, e.g., the number and type of light output events that have occurred, and the number of ultrasound events that have occurred. Statistics can also be maintained concerning total light energy output from the probe (which may be deduced from an internal optical sensor, not shown). In an embodiment, the response characteristics of the probe and the probe statistics can be available to any device 100 on which the probe 102 is mounted. Thus, for example, such characteristics and statistics can be stored in a manner that they are accessible over the Internet. In an embodiment, a VPN is used for security on the Internet.

In an embodiment where the light path 132 is fixedly attached to the probe 102, the probe usage statistics may also be relevant to the fiber optics. For example, the fibers in the light path 132 may degrade with time and/or use resulting in some loss of transmission, e.g., broken or burned fibers. Accordingly, in an embodiment, the device can maintain statistics relevant to total light energy, peak light energy and the number of pulses passed through a light path 132. In an embodiment, sensors in the probe can detect information about the energy output of the light path, and sensors in the light subsystem 129 can detect information about the energy output of the light subsystem 129. By detecting variation in the sensors at the two ends over time, maintenance issues can be identified. For example, seeing a decrease at the probe-side sensors relative to the light subsystem-side sensors may indicate a that the light path 132 is degrading and needs replacement. Moreover, a specific difference between the probe-side sensors and the light subsystem-side sensors may result in a condition that causes the device 100 to indicate that it is in need of maintenance. In an embodiment, where the difference is greater than a specific safety threshold, the device 100 may fail to continue to emit light events. In an embodiment, the information reported by these sensors may be stored with the usage statistics.

In an embodiment where the light path 132 is completely or partially detachable from the probe 102, the detachable portion of the light path may have its own unique identifier. Where the detachable portion of the light path has its own unique identifier, usage statistics that relate to that portion of the light path may be maintained in much the same manner as the usage statistics for the probe, but associated with the light path or portion.

One use of the device 100 is performing imaging examinations on humans for breast cancer detection. A clinical device 100 may be a multimodality system incorporating optoacoustic imaging capability and ultrasound imaging capability. An advantage of optoacoustic imaging over ultrasound imaging alone is that it provides very high contrast images which may provide for the direct functional evaluation of tumors.

Figure 14:
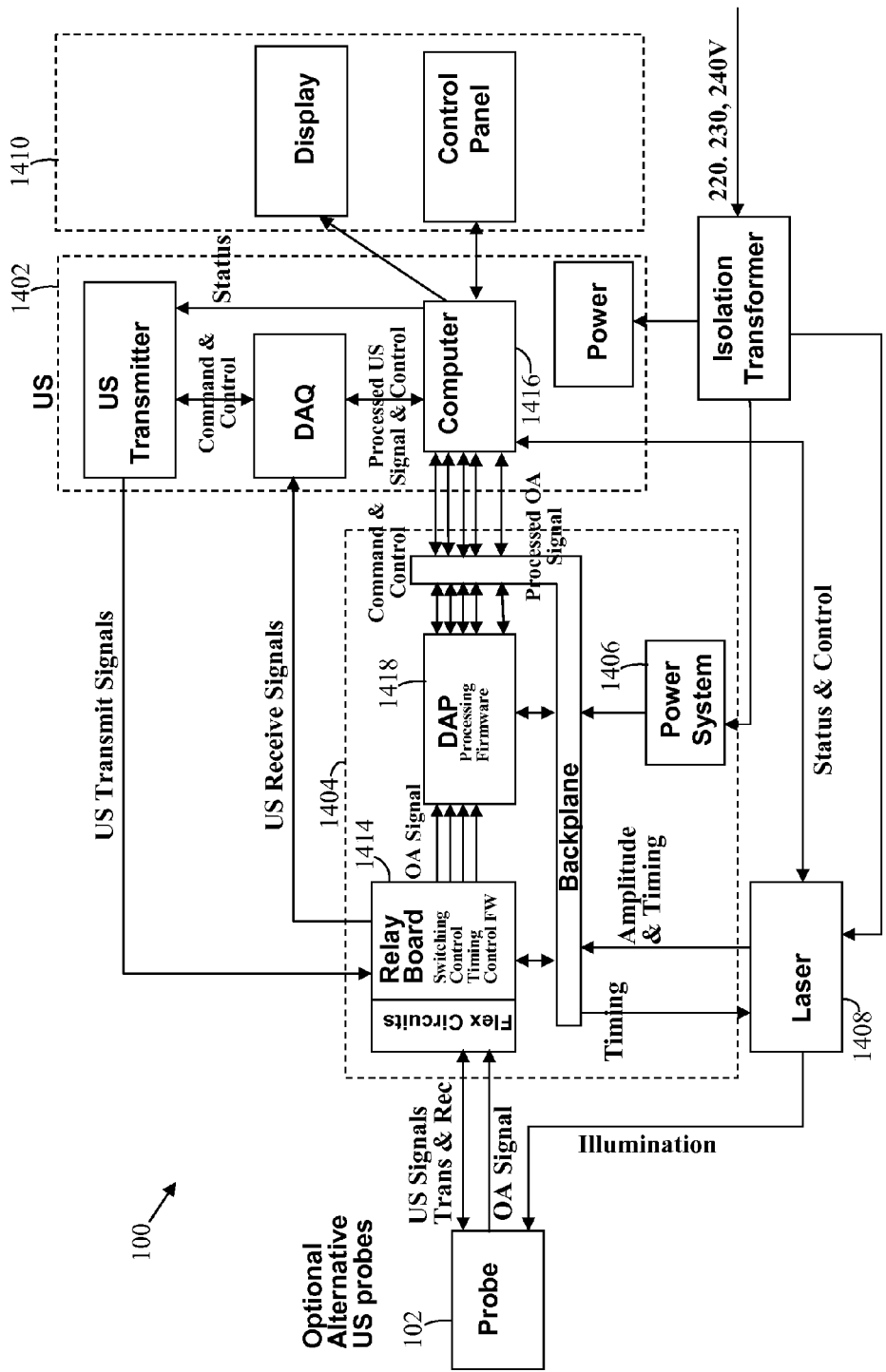
FIG. 14 is a schematic block diagram illustrating hardware components of the system.

A block diagram of an embodiment of the clinical system is shown in FIG. 14 that illustrates the interaction between major subsystems and the type of signals they represent. In an embodiment, device 100 provides an integrated system consisting of the following subsystems: ultrasound subsystem 1402, optoacoustic electronics subsystem 1404, power supply subsystem 1406, probe 102 and illumination/laser subsystem 1408, which may be housed in one console, and the control and display subsystem 1410 that can be attached to a console. The ultrasound subsystem 1402, the optoacoustic electronics subsystem 1404 and the control & display subsystem 1410 will be referred to hereinafter collectively as the UOA.

The ultrasound subsystem 1402 may be, e.g., a fully functional stand-alone ultrasound system. The ultrasound subsystem 1402 includes an ultrasound transmitter 1412 that outputs an ultrasound signal that is used to stimulate tissue. The ultrasound transmitter 1412 provides its output to a relay board 1414 in the optoacoustic electronics subsystem 1404 which switches the ultrasound signal to the probe 102. The ultrasound subsystem further includes a data acquisition board, or DAQ, that receives ultrasound signals from the relay board 1414 and processes them for transmission to and further processing by a computer 1416. The computer 1416 provides signal processing, user interface, and command and control functionality through software. The computer 1416 includes one or more computer-readable medium for storage of programming as well as data generated by the system. The computer-readable medium may be in the form of volatile and/or non-volatile RAM, ROM, solid state drive, optical media, magnetic media (e.g., hard drive) or other storage device. The memory and storage may be integrated into or physically separate from the remaining components of the computer. The computer 1416 further receives and transmits command and control signals to the DAQ for control of the data acquisition process and the ultrasound transmitter.

The optoacoustic electronics subsystem 1404 includes a relay board 1414 that provides switching functionality for alternately switching received ultrasound signals to the DAQ of the ultrasound subsystem 1402 and received optoacoustic signals to a digital acquisition and processing (DAP) board 1418. The relay board 1414 includes firmware for both switching control and timing control. In an embodiment, flex circuits that form ultrasound transducers for both transmitting and receiving ultrasound signals are integrated into the relay board 1414. The DAP 1418 receives and processes the OA signal and outputs processed OA signals to the computer 1416. The computer 1416 provides command and control signals via a backplane to the DAP 1418 and the relay board 1414, and provides timing signals via the backplane to the illumination/laser subsystem 1408.

Figure 15:
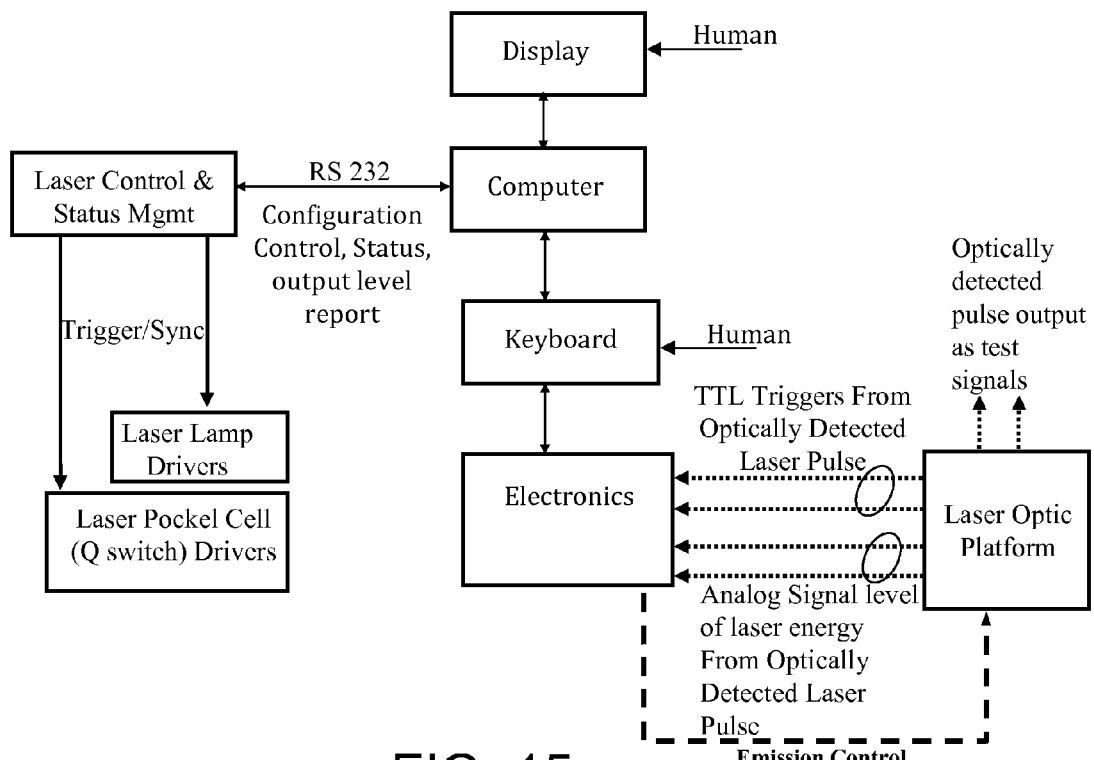
FIG. 15 is a block diagram illustrating the illumination subsystem and control interfaces of the system in accordance with an embodiment thereof.

FIG. 15 shows a block diagram illustrating the illumination subsystem 1408 and control interfaces of the system 100 in accordance with an embodiment thereof. Triggers are TTL positive for activation. Some of illumination subsystem external control and interfaces include interlocks, photo diode based outputs (6), grounds, RS232, power and optical port.

Figure 16:
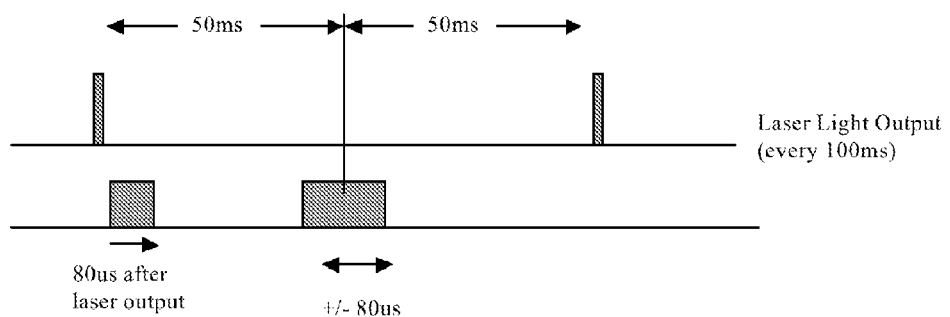
FIG. 16 is a pulse diagram illustrating a radiation restriction in the system.

FIG. 16 shows a pulse diagram illustrating a radiation restriction in the system 100.

In an embodiment the device 100 uses a hand held probe 102 including an array of transducers and an opening through which laser light can pass. In use, an operator manipulates controls and views the display as they move the probe 102 over the body or other volume to identify critical image characteristics. In an ultrasound mode the laser light source has no emission. In an optoacoustic mode the laser emits light according to specific preconfigured and/or operator set up parameters. In an embodiment the hand held probe may be manipulated in a similar fashion to the manipulation of an ultrasound probe. In an embodiment, the device 100 includes an operator selectable operational mode whereby an optoacoustic mode and ultrasound mode are interlaced.

In an embodiment the clinical device 100 includes an illumination source 1408 capable of providing two output wavelengths according to specific preconfigured and/or operator set up parameters. In an embodiment, the operator will be able to select either an Nd:YAG laser output at 1064 nm or an Alexandrite laser output at 757 nm, or to select the use of both laser outputs. When two wavelengths are selected, the laser subsystem, according to specific preconfigured and/or operator set up parameters, can alternate between to two wavelengths one after the other, or in other preconfigured or operator set up cycles. In an embodiment, laser operating parameters such as energy, pulse rate, and wavelength will be operator selectable, and subject, however, to specific preconfigured parameters.

In an embodiment, communication of the laser energy will be via a fiber optic bundle with a detachable mechanism. The detachable mechanism for interfacing the laser output to the fiber optic bundle includes a safety interlock/laser shutdown if disconnected. In an embodiment, the laser subsystem components include heat exchangers; pulse drivers; direct laser controls; laser power supplies; laser power management; laser head(s), cavities and optics; control and drive electronics; electronic interface ports; and a laser output port.

In an embodiment, the laser is completely controlled by the UOA control system. The clinical device may be powered ON/OFF by the use of a low current key switch located near the user control panel. Through the action of this low current switch, closure will cause the secondary output of an isolation transformer's 230 VAC to be applied to each of the subsystems, including the laser. Opening this switch removes power from each of the subsystems.

In an embodiment, the laser subsystem consists of a Q-Switched Nd:YAG laser and an Alexandrite Q-Switched laser with a common concentric output connector designed to have a fiber optic bundle attached. It contains all necessary electronics, cooling, power management, optics, and connections necessary to meet operational requirements.

As discussed above, according to specific preconfigured parameters, in an embodiment the operator will be able to select the clinical device 100 laser light output from the Nd:YAG (1064 nm) only or select laser light output from the Alexandrite (757 nm) only or alternating the laser light output of both wavelengths. In an embodiment, selection will be accomplished via RS232 commands from the UOA.

In an embodiment, the time between wavelength changes will preferably be less than 0.05 seconds, and the time delay to initiate the response to a wavelength change shall be less than 0.01 seconds (which is included in the 0.05 seconds to change wavelengths). This would allow a command to be 0.01 seconds before the actual wavelength change is made. These timing parameters will permit the device 100 to be capable of alternating the wavelength output at a rate up to 20 times per second so as to interleave each separate wavelength operating at 10 pulses per second.

In an embodiment, the laser output pulse width for the Nd:YAG laser is approximately 7 ns but as long as practical, and in any case should be less than 25 ns for the best pulse stability. The laser output pulse width for the Alexandrite laser may be less than approximately 60 ns and more preferably less than approximately 50 ns. In an embodiment, no satellite pulse (a secondary laser pulse occurring shortly after the primary pulse) is allowed for either laser.

The pulse rate may be operator selectable. In an embodiment, the pulse rate is operator selectable from 2, 5, 10 PPS for each wavelength, and when interlace is selected the pulse rate will double to 4, 10, 20 PPS. In an embodiment, the maximum time to select between pulse rates will be 10 seconds. The pulse rate for each laser wavelength will be independent of single wavelength or interlace operation.

In an embodiment, the energy per pulse (laser output) that will be directed into the fiber bundle will be variable between 25 mJ to 250 mJ in a minimum of 15 steps for each wavelength. In an embodiment, the control will be via the RS232 port. Energy per pulse will be independently adjustable for each wavelength. In an embodiment, the maximum time for the output energy to be affected post selection will be approximately 2 seconds.

It is desirable to minimize the unintended pulse-to-pulse variation. Accordingly, in an embodiment, the (uncontrolled) pulse-to-pulse energy variation will be less than 3% RMS from the output of either laser after 50 laser pulses.

In an embodiment, a measure of the output energy of each pulse (both wavelengths) will be made and will be communicated with an analog output pulse to the UOA. In an embodiment, the pulse will be a stretched representation of the optically detected pulse. The amplitude will be a representation of the energy of each output pulse. In an embodiment, the amplitude will be 0 to 5 V peak with 5V peak equal to the maximum energy expected. In an embodiment, the driver for these signals may be DC coupled throughout and drive a 1000 ohm termination with 0 to 5 Volts. In an embodiment, the pulse may be peak detected and stretched by at least 200 ns but the peak must occur before 2 us to permit, that at least two samples are captures, when employing a 6.8 MHz anti aliasing filter at 20 M samples/sec. In an embodiment, a 20 M samples/sec sampling unit is located in the UOA electronics. Interface connectors may use BNC on the laser subsystem. The connector output can be provided on either a single BNC connector or a pair of BNC connectors, In an embodiment, each rising edge of the laser pulses will be detected and communicated to the UOA in a TTL format over a coax cable with a BNC connector. In an embodiment, a separate signal, coax cable and connector may be used for each wavelength. In an embodiment, the signal will be a positive going TTL signal that will have a duration of at least 1 microsecond. In an embodiment, the UOA termination will be AC coupled into 50 Ohms.

In an embodiment, there will be a sync pulse jitter test. The test may use an oscilloscope with the trigger using the TTL sync pulse. The input will be the output of a wideband optical test detector that is sampling the output of the laser pulse. The RMS jitter of the optical detected waveform is preferably less than about 6 ns.

In an embodiment, each detected optical pulse for each wavelength is made available at two test connectors external to the laser system. In an embodiment, the test connectors will be BNC connectors, and the drivers for the signals should be able to drive a 50 Ohm scope load. These test signals may be used to support system testing and evaluation. In an embodiment, there is a separate output for each wavelength from the sync detectors to an analog driver for a 50 ohms output load—the amplitude can be a percentage of the actual pulse out of the optical detector.

In an embodiment, a fiber optical bundle interfaces to the output of the combined laser output port. In an embodiment, the optical output will be horizontal at the front-right of the optical unit. A quick disconnect connector may to be used to connect the fiber bundle to the laser output port.

In an embodiment, the mount for the fiber cable provides self-alignment to the laser energy output. In an embodiment, a ceramic disk with a 6 mm centered aperture will be installed at the output of the fiber optic mount to minimize damage to the fiber bundle. In an embodiment, a micro switch is engaged when the fiber bundle has made connection. The micro switch functions as a safety interlock and is used to ensure that the laser cannot be fired unless the micro switch is closed.

In an embodiment, the laser output beam shape will be circular. In an embodiment, the beam profile will be flattened to approximate a top hat shape to ensure homogeneous illumination of the optical fiber. In an embodiment, the beam width will be 6 mm in diameter at the 10% level. For safety and consistency, the beam shape should not substantially deviate from this shape; in an embodiment, the beam shape does not deviate from this shape by more than 3% RMS over time and from pulse-to-pulse.

In an embodiment, the output of each laser will be approximately 6.25 mm onto the fiber optics, and the beam should not have hot spot(s), including after extensive use. In an embodiment, both beam shapes (for the Nd:YAG and the Alexandrite) will be equal in diameter to within 5% of the 6 mm diameter. For the purposes herein, a hot spot is defined as a 15% variation in energy density over any 2 mm segment of the beam cross section. In an embodiment, the laser beam must be aimed at the output connector such that 98% of the output energy is transmitted into the fiber cable. In an embodiment, a mechanism is provided for achieving laser beam alignment in the field.

In an embodiment, the laser spectral width will be less than 30 nm at the FWHM (Full Wave Half Maximum) level, and the spectral characteristics are preferably stable and do not vary from pulse-to-pulse by more than 3 nm RMS.

In an embodiment, the major operating modes of the clinical device 100 are:

a. Off mode: where all power has been turned off and no current should be flowing within the laser subsystem. This can be accomplished by turning OFF the main circuit breaker or by turning the power key switch to off. In this case power may still be connected to the isolation transformer.

b. Sleep mode or ultrasound only mode: Almost all power is shut down for all operations but with sufficient energy to place the laser subsystem into the "on" mode. For example only the laser control unit is power up.

c. On Mode: Warm Up Period: Places all necessary power ON to allow the laser to be warmed up. The laser will measure and report to the UOA the laser head temperature. Once the laser head temperature has reached a predetermined value the UOA will place the laser system into the "standby mode". In an embodiment, the laser subsystem will not be allowed to go into the "standby mode" until sufficient warm up has occurred.

d. Standby Mode: Allows the laser to be placed into the "ready mode" quickly from a Ready Mode command.

e. Ready Mode: Places the laser into the emission mode but the shutter remains closed. In an embodiment, the emission mode can be started after 20 pulses from the emission mode command.

f. Emission mode: Provides specified output energy for as long as this mode is commanded. In this mode the laser provides for its lamp sync and driver, the Q-Switch delay and driver and the pulse rate as determined from external command. The wavelength output will be as determined from external command.

In an embodiment, the laser subsystem will have the capability to go from any operating mode to any lower operating mode directly: "off" being the lowest operating mode and "emission" being the highest operating mode. For example, in an embodiment, the operator will be able to go from the emission mode to the standby, on, sleep or off mode directly. Preferably, the operator will not be able to go from off to emission directly without first going through the modes between.

In an embodiment, the laser will operate with internal synchronism and the UOA will derive its synchronism from the laser via it sync signal outputs. In an embodiment, time sensitive interfaces (synchronism signals) will be interfaced using TTL signals, while computer interface information will be via RS232 interface. In an embodiment, the wavelength selection mode (single YAG, single ALEX, interlace mode) will be selected via RS232 and the control unit will produce the internal commands in interlace or single mode with the right timing. In an embodiment, electronics will validate the present laser emission thru energy photodiode and/or sync pulses and/or Q-Switch TTL sync outputs.

Figure 17:
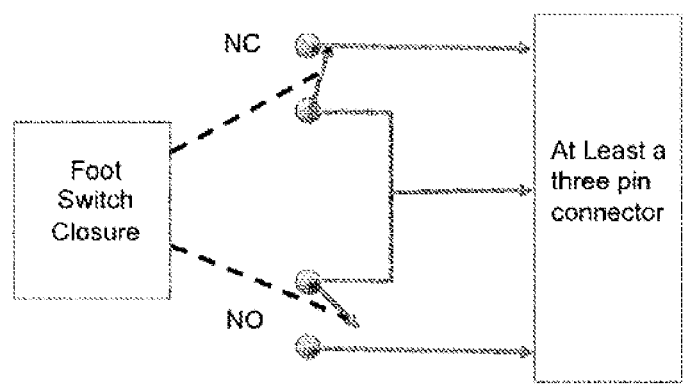
FIG. 17 is a schematic block diagram of one embodiment of a foot switch closure.

In an embodiment, a shutter will open to allow laser light to be emitted (defined as the emission mode). In an embodiment, the shutter will remain closed unless two conditions exist—a foot switch closure and an RS-232 command. But, as long as the foot switch remains closed and an RS232 command exists the emission will exist. Both the foot switch closure and the RS232 must both be present to achieve emissions. The foot switch closure may provide within the switch a double contact, NC and NO using a three-wire interface as shown in FIG. 17. When either or both the foot switch and RS232 command is changed emission will cease to exist via a closure of the shutter, preferably within about 0.5 seconds. The laser subsystem may remain in the Ready mode until commanded otherwise.

In an embodiment, the laser operating system shall keep a non-volatile time-stamped record of error codes, of lamp shots, and operational events, for the purpose of accountability and troubleshooting. The non-volatile record may be readable, and possibly erasable, via RS-232 commands. In an embodiment, erasure of the non-volatile record requires a password or other access device. In an embodiment, a log consisting of not less than 50 events may be sufficient. In an embodiment, the UOA can poll the number of messages and read them.

In an embodiment, the laser subsystem will monitor the temperature of the lasers heads and report each to the UOA on a periodic basis, permitting the UOA to avoid instructing the laser to go into the Ready Mode unless the laser head has reached an acceptable temperature, and automatically placing the laser subsystem into the off mode if the temperature is unexpectedly outside of its appropriate operating range.

In an embodiment, wires to pockels cell and all internal high radiated signals should be shielded. To mitigate electromagnetic radiation during the imaging time of the clinical device 100, the lamp driver recharging should be delayed by more than 70 microseconds after the Q-Switch. See FIG. 16. During recharge the electromagnetic radiation must be sufficiently low so as not to interfere with ultrasound or OA imaging.

In an alternative embodiment, a blanking signal can be used to suppress power supply switching noise during OA data acquisition, and also during US data acquisition, a TTL input will be supplied that a logic HIGH would cause the internal switching power supply to halt its operation of recharging the flash lamp circuits, and any other switching operation, and when at a logic LOW would resume normal operation. In an embodiment, this control may not be asserted for more than certain ON time (TBD), and to not exceed a certain duty cycle.

In an embodiment, the user interface console will contain a "Panic Button" to place the laser into the off mode by removing all AC power to the laser system.

In an embodiment, the laser subsystem and all other subsystems will operate from 230+1-10% VAC, single phases, 60/50+/−3 Hz, 3000 VA max. In an embodiment, the mains voltage may be isolated from the various subsystems by the use of an isolation transformer such as part number 925.1202, manufactured by www.toroids.com, or equivalent, and protected with a switchable AC circuit breaker on the primary side. The secondary side of this transformer will provide AC power to each of the four (4) AC powered subsystems through a soft start isolation transformer to avoid inrush current problems. In an embodiment, the laser subsystem is adapted to accommodate a sudden loss of input power or brownout without causing damage, requiring realignment, tuning or causing unsafe operations.

All operating system controls will be provided via UOA electronics.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. A method for adjusting the light output of an optoacoustic imaging system from an initial level to an operating level, the optoacoustic imaging system comprising a first light source having a light output control, a probe for delivering light to a volume, the probe being associated with one or more sensors, a light path operatively connected to the first light source, the light path providing light from the first light source to the probe, the method comprising the steps of:
 a. setting the light output control of the first light source to an initial value;
 b. pulsing the first light source, thereby delivering light to the probe and the volume;
 c. taking a measurement from the one or more sensors;
 d. changing the setting of the light output control of the first light source based upon the measurement from the one or more sensors; and
 f. repeating steps b-d until the operating level is reached.

2. The method for adjusting the light output claimed in claim 1, wherein the operating level is a predetermined level of fluence incident upon the volume.

3. The method for adjusting the light output level claimed in claim 2, wherein the step of changing the setting of the light output control comprises the steps of:
 inferring a light fluence incident upon the volume based upon the measurement from the one or more sensors;

determining a difference between the inferred fluence incident upon the volume and the predetermined level of fluence incident upon the volume;
determining a change value based upon the determined difference; and
changing the setting of the light output control of the first light source by an amount equal to the change value.

* * * * *